United States Patent
Krylov et al.

(10) Patent No.: US 11,506,660 B2
(45) Date of Patent: Nov. 22, 2022

(54) METHOD AND SYSTEM FOR DETERMINING EQUILIBRIUM DISSOCIATION CONSTANT OF A REVERSIBLE BINDING PAIR

(71) Applicant: Sergey Krylov, Toronto (CA)

(72) Inventors: Sergey Krylov, Toronto (CA); Nicolas Sisavath, Lyons (FR)

(73) Assignee: Sergey Krylov, Toronto (CA)

( * ) Notice: Subject to any disclaimer, the term of this patent is extended or adjusted under 35 U.S.C. 154(b) by 487 days.

(21) Appl. No.: 16/612,629

(22) PCT Filed: May 14, 2018

(86) PCT No.: PCT/CA2018/050568
§ 371 (c)(1),
(2) Date: Nov. 11, 2019

(87) PCT Pub. No.: WO2018/209433
PCT Pub. Date: Nov. 22, 2018

(65) Prior Publication Data
US 2020/0240985 A1    Jul. 30, 2020

Related U.S. Application Data

(60) Provisional application No. 62/506,520, filed on May 15, 2017.

(51) Int. Cl.
| | |
|---|---|
| G01N 33/557 | (2006.01) |
| B01L 3/00 | (2006.01) |
| G01N 30/22 | (2006.01) |
| G01N 30/32 | (2006.01) |
| G01N 30/72 | (2006.01) |
| G01N 30/74 | (2006.01) |
| G01N 33/68 | (2006.01) |

(52) U.S. Cl.
CPC ........ *G01N 33/557* (2013.01); *B01L 3/50273* (2013.01); *G01N 30/22* (2013.01); *G01N 30/32* (2013.01); *G01N 30/7233* (2013.01); *G01N 30/74* (2013.01); *G01N 33/6848* (2013.01); *B01L 2300/0838* (2013.01); *B01L 2300/16* (2013.01); *B01L 2400/06* (2013.01); *G01N 2030/324* (2013.01)

(58) Field of Classification Search
CPC ...... G01N 33/557; G01N 30/22; G01N 30/32; G01N 30/7233; G01N 30/74; G01N 33/6848; G01N 2030/324; B01L 2300/0838; B01L 2300/16; B01L 2400/06
See application file for complete search history.

(56) References Cited

U.S. PATENT DOCUMENTS 7,517,656 B2    4/2009    Martin et al.

FOREIGN PATENT DOCUMENTS

| EP | 2876434 | 5/2015 |
|---|---|---|
| EP | 2876434 A1 | 5/2015 |
| JP | 5633485 A | 2/2013 |
| JP | 5633485 | 12/2014 |

OTHER PUBLICATIONS

Pathare ("A Review on Various Analytical Methods Used in Determination of Dissociation Constant" Intl. J. Pharmacy and Pharmaceutical Sciences 2014 6: 26-34). (Year: 2014).*
"Capillary flow experiments for thermodynamic and kinetic characterization of protein liquid-liquid phase separation" (Stender Nature Communications 2021 12:7289). (Year: 2021).*
"ACPSF1 cooperates with terminator U-tract to dictate archaeal transcription termination efficacy" (Li eLife 2021:10e70464). (Year: 2021).*
"Comparing the epidermal growth factor interaction with four different cell lines: intriguing effects imply strong dependency of cellular context" (Bjorkelund PlosOne 6:e16536). (Year: 2011).*
L. O. Andersson, A. Rehnstrom, D. L. Eaker Eur. J. Biochem. 1971, 20, 371-380.
J. Bao, S. M. Krylova, D. J. Wilson, O. Reinstein, P. E. Johnson, S. N. Krylov, ChemBioChem 2011, 12, 2551-2554.
Bian, X. & Lockless, S.W. Anal. Chem. 2016, 88, 5549-5553.
Brautigam, C.A., Zhao, H., Vargas, C., Keller, S. & Schuck, P. Nature Protocols 2016, 11, 882.
S. M. Clark, L. Konermann, J. Am. Soc. Mass. Spectrom. 2003, 14, 430-441.
S. M. Clark, L. Konermann, Anal. Chem. 2004, 76, 7077-7083.
S. M. Clark, L. Konermann, Anal. Chem. 2004, 76, 1257-1263.
Cooper, M.A. Anal. Bioanal. Chem. 2003, 377, 834-842.
Cooper, A.M. Nat. Rev. Drug Discovery 2002, 1, 515-528.
Cottet, H. et al., Anal. Chem. 2007, 79, 9066-9073.
Draczkowski, P., Matosiuk, D. & Jozwiak, K. J. Pharm. Biomed. Anal. 2014, 87, 313-325.
Fang, Y. Expert Opin Drug Discov 2012, 7, 969-988.
A. J. Firestone, J. K. Chen, ACS Chem. Biol. 2010, 5, 15-34.
Frenzel, D. & Willbold, D., PLOS ONE 2014, 9, e106882.

(Continued)

*Primary Examiner* — Changhwa J Cheu
(74) *Attorney, Agent, or Firm* — Thomas | Horstemeyer, LLP

(57) ABSTRACT

A method and system for determining the dissociation constant ($K_d$) of a reversible binding pair of a first compound and a second compound. The method comprises: injecting a sample into a capillary tube via one or more valves, wherein the sample comprises the first compound, the second compound, and a first compound-second compound complex; injecting a mobile phase into the capillary tube via said one or more valves, the sample flowing through the capillary tube under laminar flow conditions, wherein the second compound and the first compound-second compound complex is separated from the first compound by transverse diffusion; measuring time dependence of a signal that is proportional to the concentration of the first compound, both unbound and bound to the second compound using a measurement component; and determining the equilibrium dissociation constant based on the measured signal versus time dependence.

34 Claims, 21 Drawing Sheets

(56) References Cited

OTHER PUBLICATIONS

Gruner, S. et al. Biochim. Biophys. Acta, Gen. Subj. 2014, 1840, 2843-2850.
Heegaard, N.H.H & Kennedy, R.T. Electrophoresis 1999, 20, 3122-3133.
Holyst, R. Anal. Chim. Acta 2015, 855, 51-59.
Huber, W. & Mueller, F. Current Pharmaceutical Design 2006, 12, 3999-4021.
H. Jensen, J. Østergaard, J. Am. Chem. Soc. 2010, 132, 4070-4071.
H. Imamura, T. Komori, A. Ismail, A. Suenaga, M. Otagiri, Chirality 2002, 14, 599-603.
M. Kanoatov, V. A. Galievsky, S. M. Krylova, L. T. Cherney, H. K. Jankowski, S. N. Krylov, Anal. Chem. 2015, 87, 3099-3106.
L. Konermann, J. Phys. Chem. A 1999, 103, 7210-7216.
Latunde-Dada, S., Bott,R., Hampton, K., Leszczyszyn, O.I., J. Chromatogr. A 2015, 1408, 255-260.
A. Molki, L. Khezzar, A. Goharzadeh Eur. J. Phys. 2013, 34, 1127-1134.
Nunez, S., Venhorst, J. & Kruse, C.G. Drug Discovery Today 2012, 17, 10-22.
V. Okhonin, E. Wong, S. N. Krylov, Anal. Chem. 2008, 80, 7482-7486.
Olaru, A., Bala, C., Jaffrezic-Renault, N. & Aboul-Enein, Crit. Rev. Anal. Chem. 2015, 45, 97-105.
N. N. Poulsen, N. Z. Andersen, J. Østergaard, G. Zhuang, N. J. Petersen, H. Jensen, Analyst 2015, 140, 4365-4369.
Schasfoort, R.B.M. Handbook of Surface Plasmon Resonance: 2nd Edition. (Royal Society of Chemistry, 2017) pp. 172-173 and 202.
Tellinghuisen, J. Anal. Biochem. 2003, 321, 79-88.
Tellinghuisen, J. J. Phys. Chem. B 2005, 109, 20027-20035.
Tellinghuisen, J. & Chodera, J.D. Anal. Biochem. 2011, 414, 297-299.
Wadsö, I. & Wadsö, L. J. Therm. Anal. Calorim. 2005, 82, 553-558.
F. Ye, H. Jensen, S. W. Larsen, A. Yaghmur, C. Larsen, J. Østergaard, J. Pharm. Biomed. Anal. 2012, 61, 176-183.
G. Zhuang et al., JNEMS2013, Suzhou, China 2013, 1054-10.
International Search Report and Written Opinion for PCT/CA2018/050568 dated Jul. 24, 2018.

\* cited by examiner

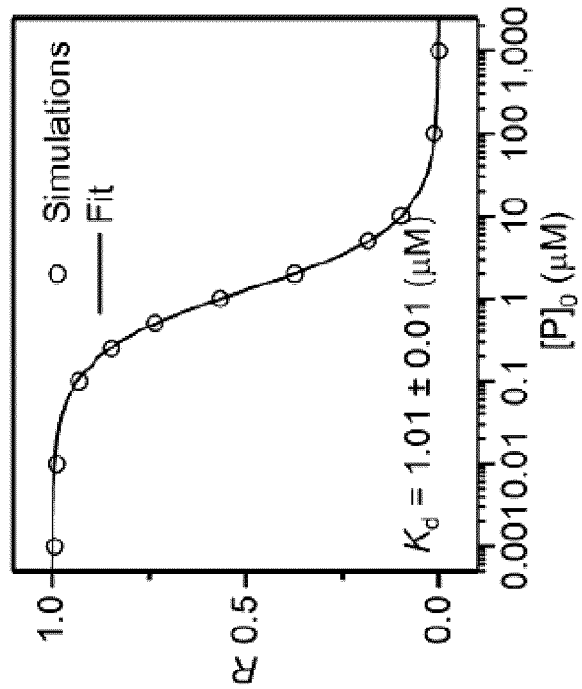
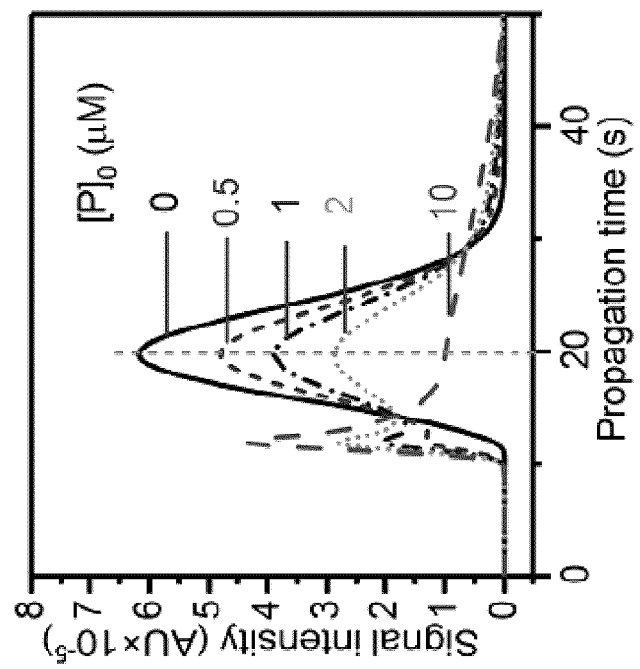
FIG. 4B
FIG. 4A

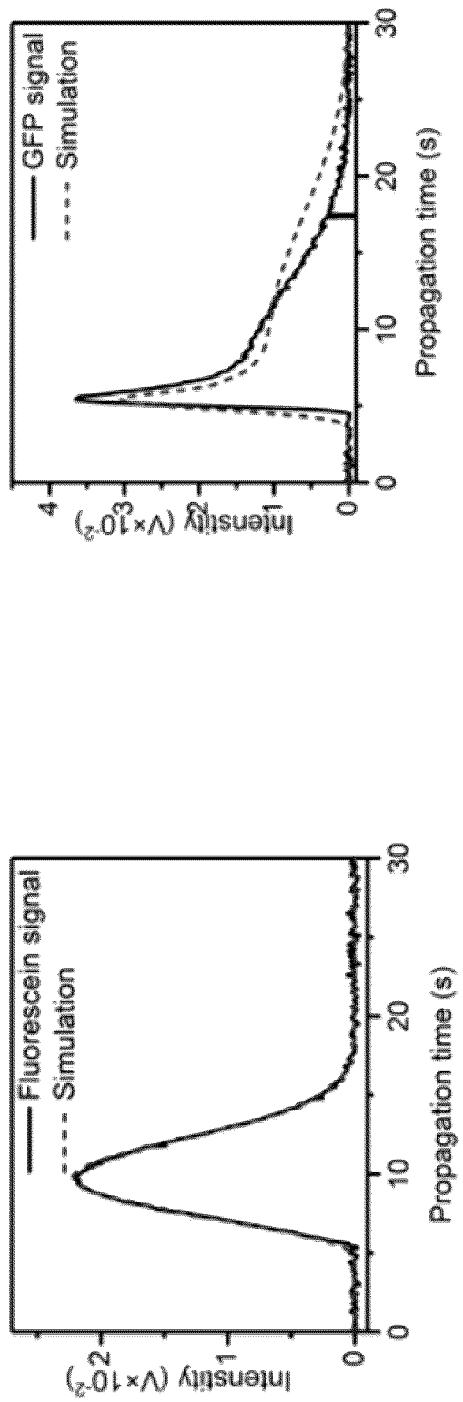
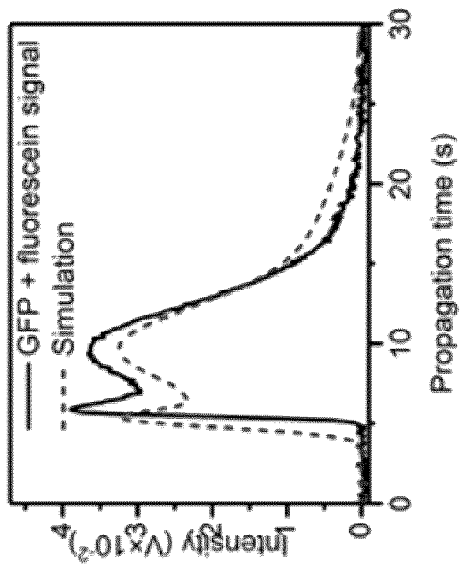
FIG. 9A
FIG. 9B
FIG. 9C

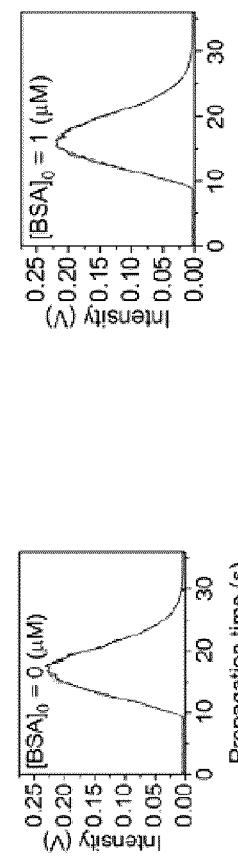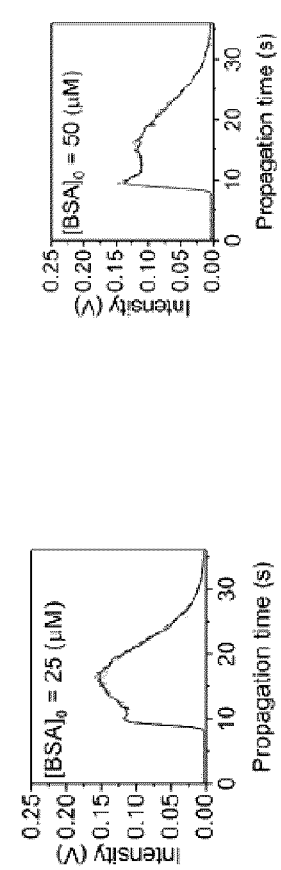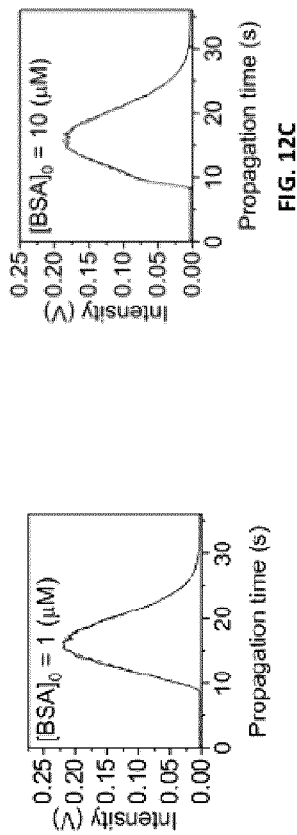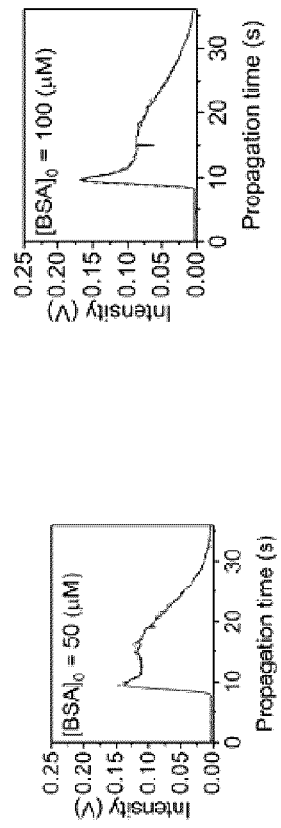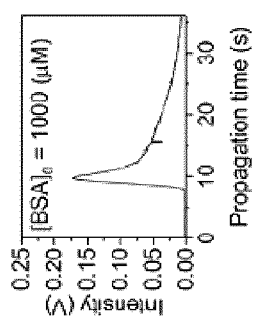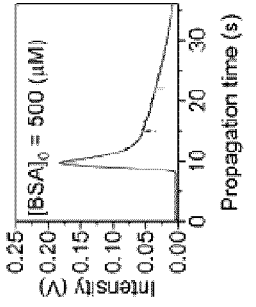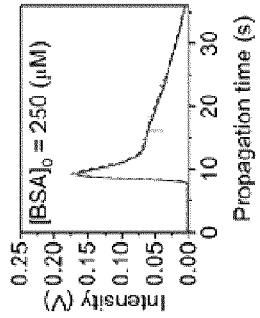

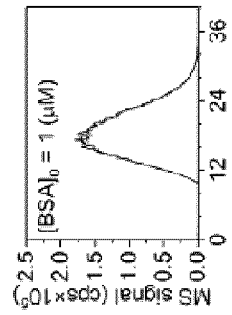
FIG. 15A
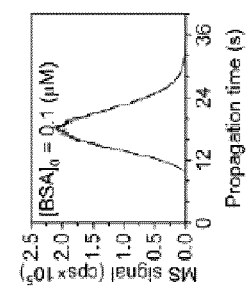
FIG. 15B
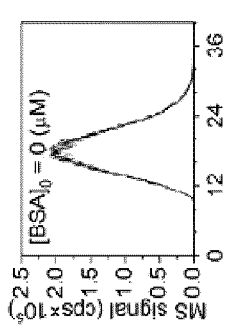
FIG. 15C
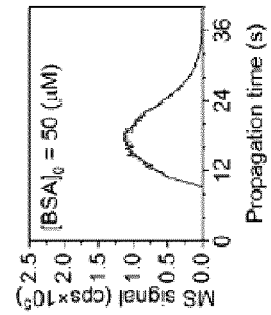
FIG. 15D
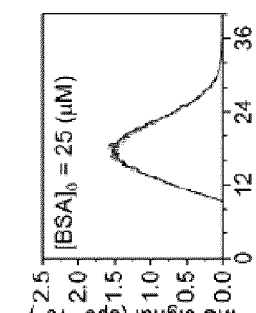
FIG. 15E
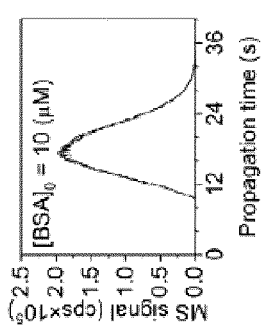
FIG. 15F
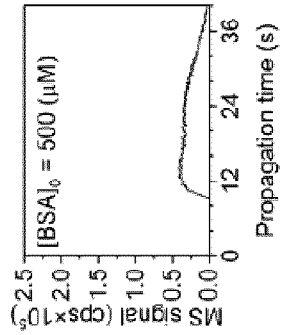
FIG. 15G
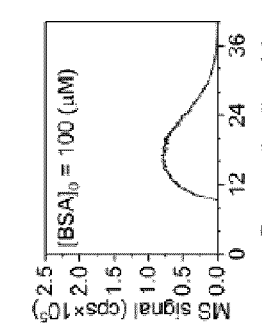
FIG. 15H
FIG. 15I

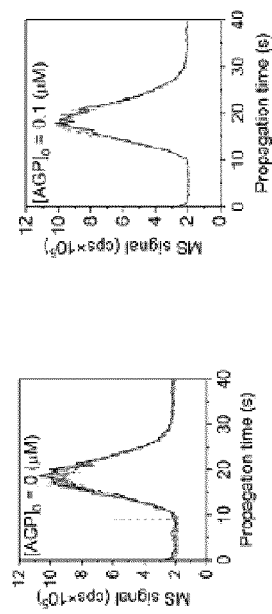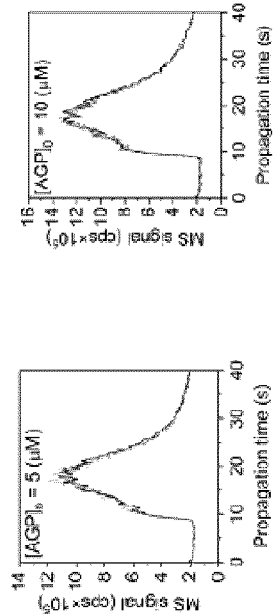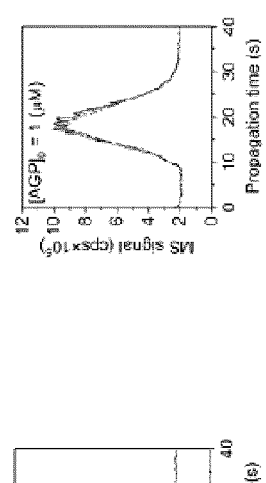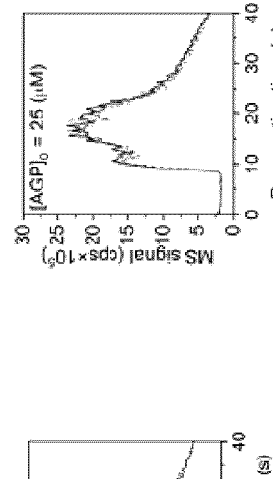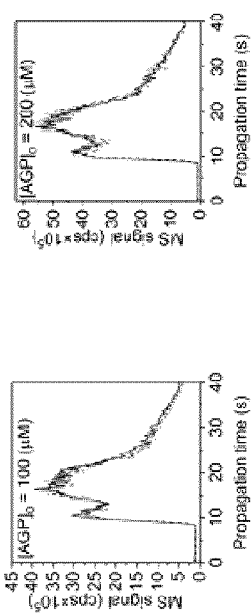

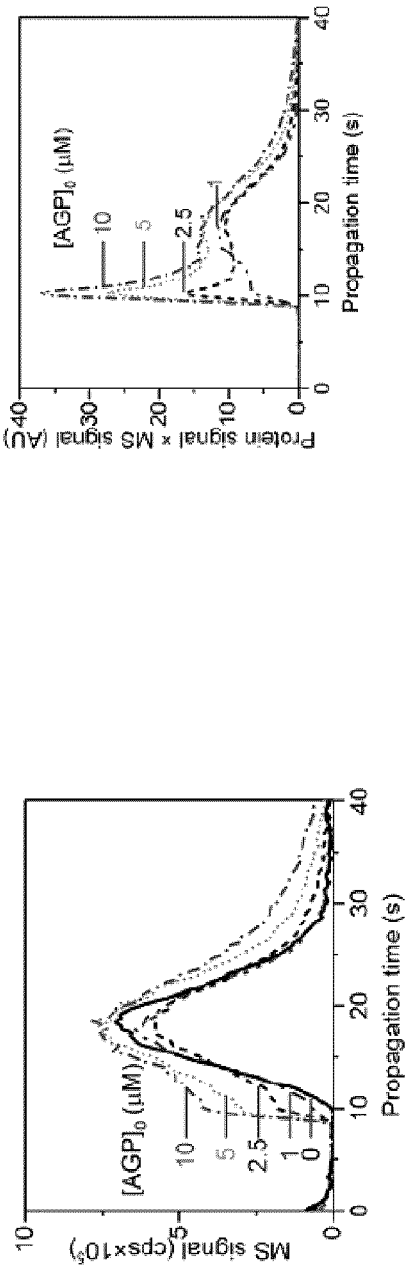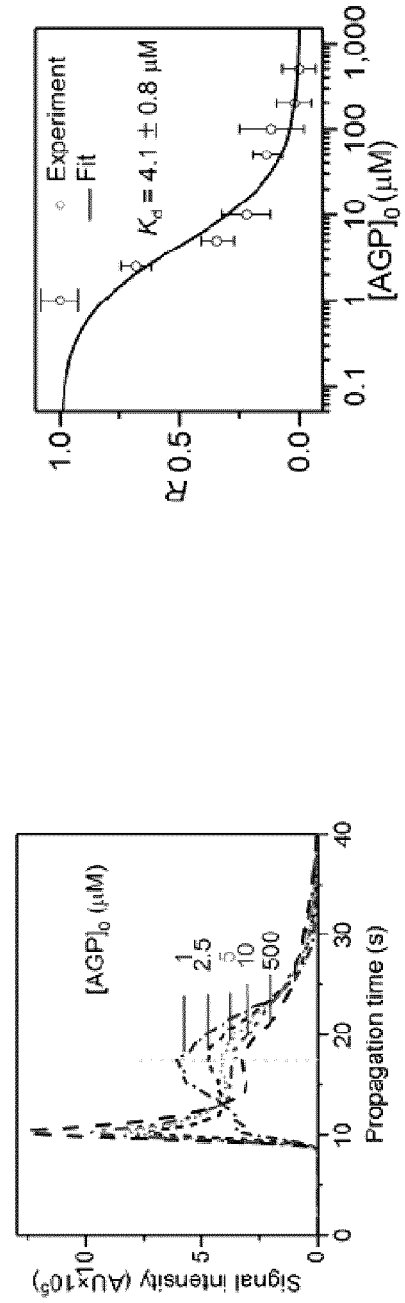
FIG. 20A
FIG. 20B
FIG. 20C
FIG. 20D

METHOD AND SYSTEM FOR DETERMINING EQUILIBRIUM DISSOCIATION CONSTANT OF A REVERSIBLE BINDING PAIR

CROSS-REFERENCE TO RELATED APPLICATIONS

This application is the 35 U.S.C. § 371 national stage application of PCT Application No. PCT/CA2018/050568, filed May 14, 2018, where the PCT claims priority to, and the benefit of, U.S. provisional application no. 62/506,520, filed May 15, 2017, both of which are herein incorporated by reference in their entireties.

FIELD

Methods and systems for determining equilibrium dissociation constant of a reversible binding pair.

BACKGROUND

Many antibodies, ligand receptors, regulatory enzymes (e.g., kinases, glycosyltransferases, and lipid transferases), and other polypeptides are considered attractive therapeutic targets. Antigens, ligands, peptides, substrates, and molecules that bind to, interact with, activate, and/or inhibit these biomolecules are considered to be potential drug candidates. High-throughput screening of combinatorial libraries of potential drug candidates is pivotal to the identification of large numbers of lead compounds for drug development.

Strong reversible binding between polypeptides (P) and molecules (SM) plays a role in biology, medicine and drug development (A. J. Firestone, J. K. Chen, *ACS Chem. Biol.* 2010, 5, 15-34). The formation of a non-covalent polypeptide-molecule complex (P-SM) is described by the following simplified chemical equation:

$$P + SM \underset{k_{off}}{\overset{k_{on}}{\rightleftharpoons}} P\text{-}SM \quad (1)$$

where $k_{on}$ and $k_{off}$ are rate constants of the forward and reverse processes, respectively.

Complex stability is characterized by the equilibrium dissociation constant $K_d$ which is defined as:

$$K_d = \frac{[SM]_{eq}[P]_{eq}}{[P\text{-}SM]_{eq}} \quad (2)$$

where $[P]_{eq}$, $[SM]_{eq}$, and $[P\text{-}SM]_{eq}$ are concentrations of P, SM and P-SM for reaction (1) being at equilibrium.

Finding $K_d$ of polypeptide-molecule binding can constitute a significant challenge due to limitations of available methods.

Fluorescence spectroscopy (e.g. fluorescence anisotropy and fluorescence correlation spectroscopy) and thermophoresis require labeling SM with a fluorophore (Cooper, M. A. *Anal. Bioanal. Chem.* 2003, 377, 834-842). It is almost impossible to not affect binding when attaching a fluorescent label to a molecule and, thus, the accuracy of $K_d$ measurements can be affected (Cooper, A. M. *Nat. Rev. Drug Discovery* 2002, 1, 515-528). Therefore, fluorescence spectroscopy and thermophoresis may be used to study polypeptide-molecule binding when the molecule is fluorescent by itself in order to obtain accurate $K_d$ measurements.

Sensor-based techniques, e.g., surface-plasmon-resonance and biolayer interferometry, require the immobilization of either SM or P on the sensor surface (Olaru, A., Bala, C., Jaffrezic-Renault, N. & Aboul-Enein, *Crit. Rev. Anal. Chem.* 2015, 45, 97-105 and Frenzel, D. & Willbold, D., *PLOS ONE* 2014, 9, e106882). Attaching SM or P to a surface is virtually impossible without affecting their binding resulting in potential loss of activity and steric accessibility (Cooper, M. A. *Nat Rev Drug Discov* 2002, 1, 515-528, Fang, Y. *Expert Opin Drug Discov* 2012, 7, 969-988 and Schasfoort, R. B. M. *Handbook of Surface Plasmon Resonance: 2nd Edition.* (Royal Society of Chemistry, 2017)). Moreover, sensor-based methods are slow because they require inside-the-instrument equilibration in reaction (1).

One example of currently used label-free and immobilization-free methods is isothermal titration calorimetry (ITC). ITC measures a fundamental thermodynamic parameter, heat enthalpy of binding reaction, and is, thus, applicable to any binding pair (Draczkowski, P., Matosiuk, D. & Jozwiak, K. *J. Pharm. Biomed. Anal.* 2014, 87, 313-325). In practice, ITC measurements are susceptible to a variety of systematic errors affecting its accuracy. In ITC, the overall system heat enthalpy rather than sole binding reaction enthalpy is quantified; this makes the results very sensitive to processes involving impurities or even sample dilution during injections (Bian, X. & Lockless, S. W. *Anal. Chem.* 2016, 88, 5549-5553 and Brautigam, C. A., Zhao, H., Vargas, C., Keller, S. & Schuck, P. *Nature Protocols* 2016, 11, 882 and Gruner, S. et al. *Biochim. Biophys. Acta, Gen. Subj.* 2014, 1840, 2843-2850. Moreover, several practical and analytical issues (calibration, gas bubbles, sorption, corrosion, statistics, etc.) contribute to the systematic error of ITC (Wadsö, I. & Wadsö, L. *J. Therm. Anal. Calorim.* 2005, 82, 553-558, Tellinghuisen, J. *Anal. Biochem.* 2003, 321, 79-88, Tellinghuisen, J. *J. Phys. Chem. B* 2005, 109, 20027-20035 and Tellinghuisen, J. & Chodera, J. D. *Anal. Biochem.* 2011, 414, 297-299). ITC is accurate as long as all systematic errors can be accounted for, which is in practice not the case. Third, measurements in ITC are slow as they require inside-the-instrument equilibration in reaction (1).

Taylor-Dispersion based methods can also be label-free and immobilization free. They require long times of sample propagation through a capillary tube and rely on the measurement of the apparent diffusion coefficient of a binding pair for the determination of $K_d$. These methods suffer from the adsorption of protein onto the inner wall of the capillary tube, thus, leading to inaccuracies in the determination of the diffusion coefficient (Latunde-Dada, S., Bott, R., Hampton, K., Leszczyszyn, O. I., *J. Chromatogr. A* 2015, 1408, 255-260). Consequently, this leads to inaccuracies in the determination of $K_d$. Additional inaccuracy of $K_d$ values measured with Taylor-Dispersion based methods may also result from an assumption that diffusion coefficient is an additive function, while it is not.

Accordingly, there is a need for an improved method and system for determining the equilibrium dissociation constant of a reversible binding pair.

SUMMARY

In one aspect there is provided a method for determining an equilibrium dissociation constant ($K_d$) of a reversible binding pair of a first compound and a second compound, the method comprising: injecting a sample into a capillary tube via one or more valves, wherein the sample comprises the first compound, the second compound, and a first compound-second compound complex; injecting a mobile phase into the capillary tube via said one or more valves, the sample flowing through the capillary tube under laminar flow conditions, wherein the second compound and the first compound-second compound complex is separated from the first compound by transverse diffusion; measuring time dependence of a signal that is proportional to the concentration of the first compound, both unbound and bound to the second compound using a measurement component; and determining the equilibrium dissociation constant based on the measured signal versus time dependence.

In another aspect, the method further comprises injecting a mobile phase into a second capillary tube, wherein the second capillary tube mimics the capillary tube, creating a constant back pressure for the mobile phase injector. In another aspect, wherein the injecting of the sample is executed by a sample injector. In another aspect, wherein the sample injector is a low-pressure pump. In another aspect, wherein the low-pressure pump is a syringe pump. In another aspect, wherein the injecting of the mobile phase is executed by a mobile phase injector. In another aspect, wherein the mobile phase injector is a high-pressure pump. In another aspect, wherein the high-pressure pump is a high-pressure liquid chromatography pump. In another aspect, wherein the injecting of the mobile phase into the second capillary tube is done using a second low pressure pump, creating a constant back pressure for the mobile phase injector and the second low pressure pump. In another aspect, wherein the $K_d$ is determined by non-linear regression of a binding isotherm with the following equation:

$$R = \frac{[SM]_{eq}}{[SM]_0} = \frac{([SM]_0 - [P]_0 - K_d) + \sqrt{([SM]_0 - [P]_0 - K_d)^2 + 4K_d[SM]_0}}{2[SM]_0}$$

wherein: R is the ratio of concentration of free first compound compared to the total concentration of the first compound in the sample; $[P]_0$ is the total second compound concentration in the sample; $[SM]_{eq}$ is the equilibrium concentration of the first compound in the sample; and $[SM]_0$ is the total concentration of the first compound in the sample. In another aspect, wherein the injecting of the sample and the injecting of the mobile phase comprises: injecting into the capillary tube the sample at a flow rate less than or about Q/10; injecting into the capillary tube the mobile phase at a flow rate less than or about Q/10 to displace the sample from the capillary tube's inlet at a distance greater than the capillary tube's diameter; and propagating the sample under the laminar flow conditions at a flow rate of $Q=\pi LD_{SM}$, wherein Q is the flow rate, L is the capillary tube's length, and $D_{SM}$ is the diffusion coefficient of the first compound. In another aspect, wherein the injecting of the sample and the injecting of the mobile phase comprises: injecting into the capillary tube the sample at a flow rate less than or about Q/10 to obtain approximately a uniform plug shape; injecting into the capillary tube a plug of a mobile phase at a flow rate less than or about Q/10 to displace the uniform plug from an inlet of the capillary tube at a distance greater than the capillary tube's diameter; and propagating the sample under the laminar flow conditions at a flow rate of $Q=\pi LD_{SM}$, wherein Q is the flow rate, L is the capillary tube's length, and $D_{SM}$ is the diffusion coefficient of the first compound. In another aspect, wherein the sample is displaced without substantively affecting the plug shape, optionally, a cylindrical plug shape. In another aspect, wherein a separation time $t_{sep}$ of the unbound first compound and the first compound bound to the second compound is determined using the formula $t_{sep}=d^2/(4D_{SM})$ wherein d is the diameter of the capillary tube, and the $D_{SM}$ is the diffusion coefficient of the first compound. In another aspect, wherein the separation time $t_{sep}$ correlates with transverse diffusion of the first compound. In another aspect, wherein the value of d is from about 10 to about 300 µm, $D_{SM}$ is from about 100 to about 1000 µm²/s, and separation time $t_{sep}$ is from about 0.025 to about 225 s. In another aspect, wherein separation time $t_{sep}$ is from about 0.2 to about 20 s. In another aspect, further comprising compensating for the second compound's effect on the signal of the first compound. In another aspect, wherein the second compound's effect on the signal of the first compound is compensated by the equation:

$$S_{ideal}=\hat{O}S_{raw}$$

wherein: $S_{ideal}$ is an adjusted signal time profile, $S_{raw}$ is a raw signal from the measurement component and:

$$\hat{O} := \hat{O}_N \hat{O}_M$$

$$\hat{O}_M = \tilde{S}_{[P]}$$

$$\hat{O}_N = \frac{\int S_{[P]=0} dt}{\int S_{raw} dt}$$

In another aspect, wherein the laminar flow conditions are maintained by pressure injection of the mobile phase into the capillary tube. In another aspect, wherein the laminar flow conditions have a flow rate from about 0.2 µL/min to about 600 µL/min, about 50 µL/min to about 400 µL/min, about 50 µL/min to about 200 µL/min, or about 50 µL/min to about 100 µL/min. In another aspect, wherein the reversible binding pair is capable of forming an equilibrium mixture of the first compound, the second compound, and a non-covalent complex of the first compound and the second compound. In another aspect, wherein the first compound is a molecule. In another aspect, wherein the molecule is a therapeutic agent. In another aspect, wherein the second compound is a polypeptide. In another aspect, wherein the polypeptide is a protein. In another aspect, wherein the polypeptide is a polypeptide is in its natural conformation. In another aspect, wherein a molecular weight of the first compound is less than the molecular weight of the second compound. In another aspect, wherein the first compound has a molecular weight less than about 1 kDa. In another aspect, wherein the second compound has a molecular weight less than about 100 kDa. In another aspect, wherein the second compound has a molecular weight from about 5 kDa to about 100 kDa. In another aspect, wherein the first compound has a diffusion coefficient that is greater than the diffusion coefficient of the second compound. In another aspect, wherein the diffusion coefficient of the first compound is at least about 2× greater than the diffusion coefficient of the second compound. In another aspect, wherein the diffusion coefficient of the first compound is at least about 5× greater than the diffusion coefficient of the second compound. In another aspect, wherein the diffusion coefficient of the first compound is at least about 8× greater than the diffusion coefficient of the second compound. In another aspect, wherein the diffusion coefficient of the first compound is from about 100 µm²/s to about 1000 µm²/s. In another aspect, wherein the diffusion coefficient of the first compound is from about 500 µm²/s to about 700 µm²/s. In another aspect, wherein the sample is an equilibrium mixture comprising the first compound, the second compound, and a first compound-second compound complex. In another aspect, wherein the measurement component is a detector. In another aspect, wherein the detector is a mass spectrometer. In another aspect, wherein the mass spectrometer comprises an atmospheric pressure chemical ionization (APCI) mass spectrometer. In another aspect, wherein the detector is optical spectrometer. In another aspect, wherein the optical spectrometer comprises light-absorbance spectrometer or a fluorescence spectrometer. In another aspect, wherein the sample further comprises a mobile phase. In another aspect, wherein the method optimizes separation of the first compound from the second compound and the first compound-second compound complex. In another aspect, wherein the mobile phase is selected to optimize separation of the first compound from the second compound and the first compound-second compound complex. In another aspect, wherein the mobile phase has a viscosity that optimizes separation of the first compound from the second compound and the first compound-second compound complex. In another aspect, wherein the second compound and the first compound-second compound complex have similar diffusion coefficients and have similar bimodal propagation profiles. In another aspect, wherein the first compound has a unimodal propagation profile. In another aspect, wherein the mobile phase is a liquid mobile phase. In another aspect, wherein the mobile phase comprises a buffer. In another aspect, wherein the mobile phase is similar to a physiological environment without compromising the detection of the first compound. In another aspect, wherein the capillary tube has an inner diameter less than about 1 mm. In another aspect, wherein the capillary tube has an inner diameter less than about 700 µm. In another aspect, wherein the capillary tube has an inner diameter less than about 400 µm, less than about 200 µm, less than about 100 µm, or less than about 50 µm. In another aspect, wherein the capillary tube has an inner diameter of from about 10 µm to about 300 µm. In another aspect, wherein the capillary tube has a length greater than about 1 cm. In another aspect, wherein the capillary tube has a length from about 1 cm to about 300 cm. In another aspect, wherein the capillary tube is one capillary tube. In another aspect, wherein the capillary tube is selected such that adsorption of the first compound, the second compound, and the first compound-second compound complex is minimized. In another aspect, wherein the capillary tube has an inner wall that is relatively smooth. In another aspect, wherein the inner wall is non-porous. In another aspect, wherein the inner wall is coated with a flexible coating material. In another aspect, wherein the material is fused silica, a polymer, and/or resin. In another aspect, wherein the material is selected from the group consisting of polyimide, silicone, polyacrylate, aluminum, fluoropolymer, polystyrene, fused silica, polymethylmethacrylate, fluoroplastic, and acrylic. In another aspect, wherein the capillary tube has a length L that is proportional to a flow rate Q under the laminar flow conditions, wherein the proportion is determined by the formula $Q=\pi L D_{SM}$, where $D_{SM}$ is the diffusion coefficient of the first compound. In another aspect, wherein the capillary tube has a diameter d greater than $\rho L D_{SM}/(500\eta)$ when Reynolds number is less than about 2000, wherein $\rho$ and $\eta$ are the density and dynamic viscosity of the mobile phase injected into the capillary tube to maintain laminar flow conditions, respectively. In another aspect, wherein the mobile phase is injected continuously under constant pressure into the capillary tube. In another aspect, wherein the mobile phase is injected at a pressure from about 0.2 psi to about 3000 psi. In another aspect, wherein the method is suitable for high throughput screening. In another aspect, wherein the method is suitable for screening the first compound or the second compound for their ability to form a first compound-second compound complex. In another aspect, wherein said one or more valves are two valves. In another aspect, further comprising injecting the sample through an injector loop. In another aspect, wherein the first compound and the second compound are both polypeptides. In another aspect, wherein the first compound and the second compound are both proteins.

In yet another aspect, there is provided a system for determining an equilibrium dissociation constant ($K_d$) of a reversible binding pair of a first compound and a second compound, comprising: a capillary tube; a sample injector configured for injecting a sample into the capillary tube, the sample comprising the first compound, the second compound, and the first compound-the second compound complex; a mobile phase injector configured for injecting a mobile phase into the capillary tube; one or more valves controlling the sample injector and the mobile phase injector, the one or more valves configured to allow injection of the sample under laminar flow conditions within the capillary tube and separation of the second compound and the first compound-second compound complex from the first compound by transverse diffusion within the capillary tube; and a measurement component configured for measuring time dependence of the signal that is proportional to the concentration of the first compound, both unbound and bound to the second compound.

In another aspect, wherein said one or more valves are operated by a controller. In another aspect, wherein the controller is a processor programmed to operate said one or more valves. In another aspect, wherein the sample injector is a low-pressure pump. In another aspect, wherein the low-pressure pump is a syringe pump. In another aspect, wherein the mobile phase injector is a high-pressure pump. In another aspect, wherein the high-pressure pump is a high-pressure liquid chromatography pump. In another aspect, further comprising a second mobile phase injector configured for injecting a mobile phase into a second capillary tube, wherein the second capillary tube mimics the capillary tube and creates a constant back pressure for the mobile phase injector. In another aspect, further comprising a second mobile phase injector configured for injecting a mobile phase using a second low pressure pump into a second capillary tube, wherein the second capillary tube mimics the capillary tube and creates a constant back pressure for the mobile phase injector and the second low pressure pump. In another aspect, wherein the $K_d$ is determined by non-linear regression of a binding isotherm with the following equation:

$$R = \frac{[SM]_{eq}}{[SM]_0} = \frac{([SM]_0 - [P]_0 - K_d) + \sqrt{([SM]_0 - [P]_0 - K_d)^2 + 4K_d[SM]_0}}{2[SM]_0}$$

wherein:
R is the ratio of concentration of free first compound compared to the total concentration of the first compound in the sample; $[P]_0$ is the total second compound concentration in the sample; $[SM]_{eq}$ is the equilibrium concentration of the first compound in the sample; and $[SM]_0$ is the total concentration of the first compound in the sample. In another aspect, wherein the controller is programmed to instruct the one or more valves as follows: allow the sample injector to inject, into the capillary tube, the sample at a flow rate less than or about Q/10; allow the mobile phase injector to inject, into the capillary tube, the mobile phase at a flow rate less than or about Q/10 to displace the sample from the capillary tube's inlet at a distance greater than the capillary tube's diameter; and allow the mobile phase injector to propagate the sample under laminar flow conditions at a flow rate of $Q=\pi L D_{SM}$, wherein Q is the flow rate, L is the capillary tube's length, and $D_{SM}$ is the diffusion coefficient of the first compound. In another aspect, wherein the controller is programmed to instruct the one or more valves as follows: allow the sample injector to inject, into the capillary tube, the sample at a flow rate less than or about Q/10 to obtain approximately, a uniform plug shape; allow the mobile phase injector to inject, into the capillary tube, a plug of a mobile phase at a flow rate less than or about Q/10 to displace the uniform plug from an inlet of the capillary tube at a distance greater than the capillary tube's diameter; and allow the mobile phase injector to propagate the sample under laminar flow conditions at a flow rate of $Q=\pi L D_{SM}$, wherein Q is the flow rate, L is the capillary tube's length, and $D_{SM}$ is the diffusion coefficient of the first compound. In another aspect, wherein the sample is displaced without substantively affecting the plug shape, optionally, a cylindrical plug shape. In another aspect, wherein a separation time $t_{sep}$ of the unbound first compound and the first compound bound to the second compound is determined using the formula $t_{sep}=d^2/(4D_{SM})$ wherein d is the diameter of the capillary tube, and the $D_{SM}$ is the diffusion coefficient of the first compound. In another aspect, wherein the separation time $t_{sep}$ correlates with transverse diffusion of the first compound. In another aspect, wherein the value of d is from about 10 to about 300 μm, $D_{SM}$ is from about 100 to about 1000 μm$^2$/s, and separation time $t_{sep}$ is from about 0.025 to about 225 s. In another aspect, wherein separation time $t_{sep}$ is from about 0.2 to about 20 s. In another aspect, wherein the system compensates for the second compound's effect on the signal of the first compound. In another aspect, wherein the controller is configured to compensate for the second compound's effect on the signal of the first compound. In another aspect, wherein the second compound's effect on the signal of the first compound is compensated by the equation:

$$S_{ideal}=\hat{O}S_{raw}$$

wherein: $S_{ideal}$ is an adjusted signal time profile, $S_{raw}$ is a raw signal from the measurement component and:

$$\hat{O}:=\hat{O}_N\hat{O}_M$$

$$\hat{O}_M=\tilde{S}_{[P]}$$

$$\hat{O}_N=\frac{\int S_{[P]=0}dt}{\int S_{raw}dt}$$

In another aspect, wherein the laminar flow conditions are maintained by pressure injection of the mobile phase into the capillary tube. In another aspect, wherein the laminar flow conditions have a flow rate from about 0.2 μL/min to 600 μL/min, about 50 μL/min to about 400 μL/min, about 50 μL/min to about 200 μL/min, or about 50 μL/min to about 100 μL/min. In another aspect, wherein the reversible binding pair is capable of forming an equilibrium mixture of the first compound, the second compound, and a non-covalent complex of the first compound and the second compound. In another aspect, wherein the first compound is a molecule. In another aspect, wherein the molecule is a therapeutic agent. In another aspect, wherein the second compound is a polypeptide. In another aspect, wherein the polypeptide is a protein. In another aspect, wherein the polypeptide is a polypeptide is in its natural conformation. In another aspect, wherein a molecular weight of the first compound is less than the molecular weight of the second compound. In another aspect, wherein the first compound has a molecular weight less than about 1 kDa. In another aspect, wherein the second compound has a molecular weight less than about 100 kDa. In another aspect, wherein the second compound has a molecular weight from about 5 kDa to about 100 kDa. In another aspect, wherein the first compound has a diffusion coefficient that is greater than the diffusion coefficient of the second compound. In another aspect, wherein the diffusion coefficient of the first compound is at least about 2× greater than the diffusion coefficient of the second compound. In another aspect, wherein the diffusion coefficient of the first compound is at least about 5× greater than the diffusion coefficient of the second compound. In another aspect, wherein the diffusion coefficient of the first compound is at least about 8× greater than the diffusion coefficient of the second compound. In another aspect, wherein the diffusion coefficient of the first compound is from about 100 μm$^2$/s to about 1000 μm$^2$/s. In another aspect, wherein the diffusion coefficient of the first compound is from about 500 μm$^2$/s to about 700 μm$^2$/s. In another aspect, wherein the sample is an equilibrium mixture comprising the first compound, the second compound, and a first compound-second compound complex. In another aspect, wherein the measurement component is a detector. In another aspect, wherein the detector is a mass spectrometer. In another aspect, wherein the mass spectrometer comprises an atmospheric pressure chemical ionization (APCI) mass spectrometer. In another aspect, wherein the detector is optical spectrometer. In another aspect, wherein the optical spectrometer comprises light-absorbance spectrometer or a fluorescence spectrometer. In another aspect, wherein the sample further comprises a mobile phase. In another aspect, wherein the method optimizes separation of the first compound from the second compound and the first compound-second compound complex. In another aspect, wherein the mobile phase is selected to optimize separation of the first compound from the second compound and the first compound-second compound complex. In another aspect, wherein the mobile phase has a viscosity that optimizes separation of the first compound from the second compound and the first compound-second compound complex. In another aspect, wherein the second compound and the first compound-second compound complex have similar diffusion coefficients and have similar bimodal propagation profiles. In another aspect, wherein the first compound has a unimodal propagation profile. In another aspect, wherein the mobile phase is a liquid mobile phase. In another aspect, wherein the mobile phase comprises a buffer. In another aspect, wherein the mobile phase is similar to a physiological environment without compromising the detection of the first compound. In another aspect, wherein the capillary tube has an inner diameter less than about 1 mm. In another aspect, wherein the capillary tube has an inner diameter less than about 700 μm. In another aspect, wherein the capillary tube has an inner diameter less than about 400 μm, less than about 200 μm, less than about 100 μm, or less than about 50 μm. In another aspect, wherein the capillary tube has an inner diameter of from about 10 μm to about 300 μm. In another aspect, wherein the capillary tube has a length greater than about 1 cm. In another aspect, wherein the capillary tube has a length from about 1 cm to about 300 cm. In another aspect, wherein the capillary tube is one capillary tube. In another aspect, wherein the capillary tube is selected such that adsorption of the first compound, the second compound, and the first compound-second compound complex is minimized. In another aspect, wherein the capillary tube has an inner wall that is relatively smooth. In another aspect, wherein the inner wall is non-porous. In another aspect, wherein the inner wall is coated with a flexible coating material. In another aspect, wherein the material is fused silica, a polymer, and/or resin. In another aspect, wherein the material is selected from the group consisting of polyimide, silicone, polyacrylate, aluminum, fluoropolymer, polystyrene, fused silica, polymethylmethacrylate, fluoroplastic, and acrylic. In another aspect, wherein the capillary tube has a length L that is proportional to a flow rate Q under the laminar flow conditions, wherein the proportion is determined by the formula $Q=\pi LD_{SM}$, where $D_{SM}$ is the diffusion coefficient of the first compound. In another aspect, wherein the capillary tube has a diameter d greater than $\rho LD_{SM}/(500\eta)$ when Reynolds number is less than about 2000, wherein $\rho$ and $\eta$ are the density and dynamic viscosity of the mobile phase injected into the capillary tube to maintain laminar flow conditions, respectively. In another aspect, wherein the mobile phase is injected continuously under constant pressure into the capillary tube. In another aspect, wherein the mobile phase is injected at a pressure from about 0.2 psi to about 3000 psi. In another aspect, wherein the method is suitable for high throughput screening. In another aspect, wherein the method is suitable for screening the first compound or the second compound for their ability to form a first compound-second compound complex. In another aspect, wherein said one or more valves are two valves. In another aspect, further comprising an injector loop for sample injection. In another aspect, wherein the first compound and the second compound are both polypeptides. In another aspect, wherein the first compound and the second compound are both proteins.

In another aspect, there is provided the method described herein for use with the system described herein. In other aspects, wherein the $K_d$ is at least about 1 nM. In other aspects, wherein the $K_d$ is from about 1 nM to about 40 μM.

Additional aspects will be apparent in view of the description which follows. Other features and advantages will be apparent from the specification and the claims.

BRIEF DESCRIPTION OF THE DRAWINGS

Features and advantages of embodiments will become apparent from the following detailed description, taken in combination with the appended drawings in which:

FIGS. 1A-D illustrate a simulation of $K_d$ determination by LSTDLPF according to an embodiment in which FIG. 1A illustrates the shapes of the equilibrium mixture (EM), SM, P, and P-SM within the capillary tube with laminar pipe flow (LPF) conditions; FIG. 1B illustrates temporal propagation profiles of SM, P, and P-SM at the capillary tube's outlet; FIG. 1C illustrates six simulated temporal propagation profiles of [SM]+[P-SM] at constant $[SM]_0=0.5$ μM while varying $[P]_0$ in EM; and FIG. 1D is the binding isotherm obtained using the data illustrated in FIG. 1C.

FIG. 2A illustrates temporal propagation profiles of SM+P-SM at the outlet of the capillary tube; and FIG. 2B illustrates a binding isotherm obtained from the data illustrated in FIG. 2A.

FIG. 3A illustrates temporal propagation profiles of SM+P-SM at the outlet of the capillary tube; and FIG. 3B illustrates a binding isotherm obtained from the data illustrated in FIG. 3A.

FIGS. 4A and 4B illustrate the effect of fluorescence quenching ($\alpha=0.5$) on accuracy of $K_d$ determination by LSTDLPF-based methods according to embodiments. FIG. 4A illustrates temporal propagation profiles of SM+P-SM at the outlet of the capillary tube; and FIG. 4B illustrates a binding isotherm obtained from the data illustrated in FIG. 4A.

FIG. 5A illustrates temporal propagation profiles of SM+P-SM at the outlet of the capillary tube; FIG. 5B illustrates the screening-affected signals.

FIGS. 6A-6C illustrate conformity between simulated curves (dotted lines) and experimental results (solid lines) obtained by a commercial capillary-electrophoresis instrument for the pair of green fluorescent protein and fluorescein in which FIG. 6A illustrates the signal obtained when $[fluorescein]_0=1\times10^{-8}$ M; FIG. 6B illustrates the signal obtained when $[GFP]_0=4.63\times10^{-7}$ M (12.5 mg/L); and FIG. 6C illustrates the signal obtained for GFP/fluorescein mixture injected at $[fluorescein]_0=1\times10^{-8}$ M and $[GFP]_0=4.63\times10^{-7}$ M.

FIGS. 8A-8C illustrate the control scheme of valves for a system for determining the equilibrium dissociation constant of a reversible binding pair of a polypeptide and molecule according to one embodiment in which FIG. 8A illustrates filling of the injection loop; FIG. 8B illustrates injection of the EM sample at the injection flow rate followed by a plug of mobile phase; and FIG. 8C illustrates propagation of the EM at the propagation flow rate and fast separation between SM and P-SM.

FIGS. 9A-9C illustrate conformity between simulated curves (dotted lines) and experimental results (sold lines) obtained by a system for determination of the equilibrium dissociation constant, for the pair of green fluorescent protein and fluorescein in which FIG. 9A illustrates the signal obtained when $[fluorescein]_0=1\times10^{-7}$ M; FIG. 9B illustrates the signal obtained when $[GFP]_0=4.63\times10^{-7}$ M (12.5 mg/L);

and FIG. 9C illustrates the signal obtained for GFP-fluorescein mixture injected at $[\text{fluorescein}]_0=1\times10^{-7}$ M and $[\text{GFP}]_0=4.63\times10^{-7}$ M.

FIG. 11A illustrates temporal propagation profiles obtained from the fluorescence signal of fluorescein of a set $[\text{fluorescein}]_0=2\times10^{-7}$ M, while varying $[\text{BSA}]_0$ in the equilibrium mixture; and FIG. 11B illustrates the fraction of unbound fluorescein determined using equation 4 (as described below) from data illustrated in FIG. 11A as a function of $[\text{BSA}]_0$ and the binding isotherm (solid line) is obtained by a non-linear regression fitting of experimental points using equation 5 (as described below).

FIGS. 12A-12I illustrate reproducibility of experimental results for fluorescein/BSA interaction studies according to an embodiment using fluorescence detection mode with 3 repetitions at each $[\text{BSA}]_0$ ranging from 0 to 1000 μM.

FIG. 14A illustrates temporal propagation profiles at fixed fluorescein concentration where $[\text{fluorescein}]_0=2\times10^{-7}$ M and varying BSA concentrations; FIG. 14B illustrates temporal propagation profiles after the application of the compensation; and FIG. 14C illustrates the fraction of unbound fluorescein (empty circles) determined using equation 4 (as described below) from data illustrated in FIG. 14B and the binding isotherm (solid line) is obtained by a non-linear regression fitting of experimental points using equation 5 (as described below).

FIGS. 15A-15I illustrate reproducibility of experimental results for fluorescein/BSA interaction studies using mass-spectrometry detection mode according to embodiments with 3 repetitions at each $[\text{BSA}]_0$ ranging from 0 to 500 μM, respectively.

FIG. 16A illustrates temporal propagation profiles at fixed alprenolol concentration where $[\text{alprenolol}]_0=5\times10^{-7}$ M and varying AGP concentrations; FIG. 16B illustrates temporal propagation profiles after the application of the compensation; and FIG. 16C illustrates the experimental binding isotherm and the exemplary non-linear regression using equation 5 (as described below).

FIG. 17A displays the simulated protein signal utilized to multiply the experimental signals; and FIG. 17B displays products of the multiplication.

FIG. 18A illustrates fluorescein temporal propagation profiles; FIG. 18B illustrates products of multiplication of the experimental signals and the simulated protein signal; FIG. 18C illustrates products of multiplication of experimental signals and the simulated protein signal normalized to the area of the curve at $[\text{BSA}]_0=0$; and FIG. 18D illustrates a binding isotherm obtained from data illustrated in FIG. 18C with the line found by non-linear regression of the data points with equation 5 (as described below).

FIGS. 19A-19J illustrate reproducibility of experimental results for alprenolol/AGP interaction studies by LSTDLPF using mass-spectrometry detection mode according to embodiments with 3 repetitions at $[\text{AGP}]_0$ ranging from 0 to 200 μM, respectively.

FIGS. 20A-20D illustrate signal compensation procedures applied to alprenolol/AGP signals obtained by LSTDLPF using mass-spectrometry detection according to embodiments. FIG. 20A illustrates alprenolol temporal propagation profiles; FIG. 20B illustrates products of multiplication of the experimental signals and the simulated protein signal; FIG. 20C illustrates multiplication products between experimental signal and the simulated protein signal normalized to the area of the curve at $[\text{AGP}]_0=0$; and FIG. 20D illustrates a binding isotherm obtained from data illustrated in FIG. 20C with the line found by non-linear regression of the data points with equation 5 (as described below).

FIGS. 21A-21B illustrate a simulation of $K_d$ determination by LSTDLPF according to an embodiment in which FIG. 21A illustrates five simulated temporal propagation profiles of $[\text{SM}]+[\text{P-SM}]$ at constant $[\text{SM}]_0=0.5$ μM while varying $[\text{P}]_0$ in EM and FIG. 21B is the binding isotherm obtained using the data illustrated in FIG. 21A, where the diffusion coefficient of SM was 2× larger than that of P and P-SM.

DETAILED DESCRIPTION OF THE EMBODIMENTS

Figure 1B:
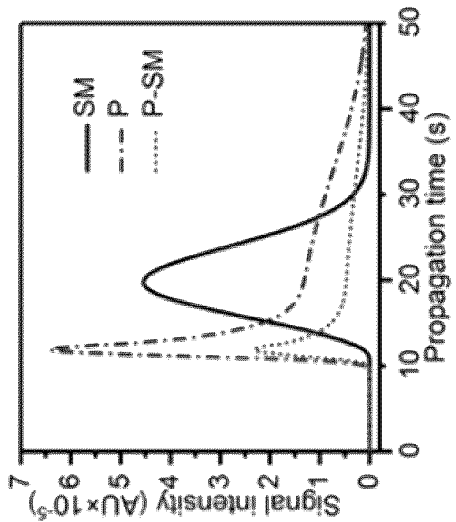

The description which follows and the embodiments described therein are provided by way of illustration of an example or examples of particular embodiments of the principles of the present invention. These examples are provided for the purposes of explanation and not limitation of those principles and of the invention.

As used herein, the terms "capillary tube" and "capillary" is used broadly herein to denote any open channel having opposite open ends (i.e., an inlet and outlet) such that fluid can be passed through the length of the channel. The capillary can, for example, include any hollow tube, as well as any channel, column, conduit, passage, etc., that permits the flow of a liquid or gas, typically under specified conditions (e.g., of temperature, pressure, etc.). The capillary may comprise any suitable material known to those skilled in the art for capillaries. For example, Teflon, metal or any other typical material that is bendable for easy connection to a detector. Typically, a capillary has a small inner diameter (e.g., less than about 1 mm). The capillary tube of the methods and system described herein may have any length and diameter satisfying laminar flow conditions but is typically of a size to permit handling of picoliter to microliter volumes of fluid. The capillary tube has at least two ends (i.e., an inlet and outlet), but may have more if bifurcated or branched. In one embodiment, the capillary tube is a preformed channel in a microfabricated device or chip (e.g., a "lab on a chip"). In some embodiments the channel is round (tubular), the cross section is generally circular and the cross-sectional area is simply the area of the circle defined by the channel cross section (area=$\pi r^2$). For example, the capillaries have smaller internal diameters, e.g., less than about 1 mm, less than about 700 µm, less than about 400 µm, less than about 200 µm, less than about 100 µm, or less than about 50 µm.

Some embodiments involve the use of a capillary having any suitable length for determining $K_d$. For example, lengths can include lengths greater than 5 cm, and typically from about 1 cm to about 300 cm. In some embodiments, the capillary is an individual stretch of conventional capillary tubing. In other embodiments, the capillary can assume other formats, so long as it includes a channel satisfying the structural and functional criteria set forth herein. Examples include a capillary tube, a bundle of tubes, a solid block or chip having one or more passageways or flow cells running therethrough, e.g., a microfluidics device such as those associated with BiaCore, Inc. (Piscataway, N.J.), Gyros, Inc. (Uppsala, Sweden), Caliper Technologies, Inc. (Mountain View, Calif.) and the like. The passageways can have linear or non-linear central axes, e.g., they can be coiled, curved or straight. The cross-sectional geometry of the passageway is not critical, so long as it allows the channel to function as an extraction channel. For example, capillary tubes having a round cross-sectional geometry work well and can be purchased from a number of vendors. However, other geometries, such as oval, rectangular or another polygonal shape, or a combination of such shapes, can also be employed. The structure and configuration of the capillary can assume any of a wide variety of configurations, including but not limited to single and multi-lumen capillaries, such as those available from Paradigm Optics, Inc. (Vancouver, Wash.). The capillary can be provided as a single capillary, multiple capillaries linked in sequence, or as part of a bundle or array of distinct capillary channels. In typical embodiments, the inner wall(s) of the capillary is relatively smooth such that adsorption of the reversible binding pair is minimized. More typically, the wall(s) are non-porous. In embodiments, the capillary can be beneficially coated with a flexible coating material, typically fused silica, a polymer or resin. Typical coating materials include polyimide, silicone, polyacrylate, aluminum or fluoropolymer, fused silica, polystyrene, polymethylmethacrylate, fluoroplastic, and acrylic.

A capillary, or capillary tube, may be considered a microreactor. If analysis requires a chemical reaction, e.g. labeling followed by separation in a capillary, the reaction can be done inside the capillary with very small volumes of reactants for analytical applications. Reactions in the capillary can be carried out in nanoliter volumes. In addition, the capillary can be easily interfaced with optical, electrochemical, and mass-spectrometric detectors, thereby offering analytical capabilities. It is known in the relevant art that a particular volume of liquid introduced into a capillary may be referred to as a "plug". Accordingly, in the methods and system described herein, fluids may be introduced into the capillary as a plug of fluid.

As used herein, the term "reversible binding pair" refers to two compounds (e.g. a first compound and a second compound) that specifically bind to one another in a non-covalent manner to form a first compound-second compound complex. The reversible binding pair is capable of forming an equilibrium mixture of the first compound, the second compound, and a non-covalent complex of the first compound and the second compound.

As used herein, the terms "first compound" and "second compound" include, for example, any compounds/molecules, wherein the molecular weight of the first compound is less than the molecular weight of the second compound. Some typical embodiments include first compounds with less than about 1 kDa and second compounds having less than about 100 kDa and, more specifically, from about 5 kDa to about 100 kDa. In other examples, the first compound includes a compound/molecule that has a diffusion coefficient that is greater than the diffusion coefficient of the second compound. In embodiments, the first compound has a diffusion coefficient that is an order of magnitude larger than the diffusion coefficient of the second compound. In some embodiments, the diffusion coefficient of the first compound is at least about 2× (i.e. two times) greater than that of the second compound, which also correlates to the first compound having a molecular weight that is at least about 8× (i.e. eight times) lower than the molecular weight of the second compound. In other embodiments, the diffusion coefficient of the first compound is at least about 5× (i.e. five times) greater than that of the second compound. In further embodiments, the diffusion coefficient of the first compound is at least about 8× greater than that of the second compound.

Some examples of reversible binding pairs include a receptor (e.g., enzyme) and a ligand; an antibody and an antigen; complementary nucleic acids; or an aptamer and its target. "Nucleic acids" may be any natural or synthetic nucleic acids, including DNA and RNA, and can be from 10 to 1,000 nucleotides in length. In certain embodiments, the nucleic acids are 10 to 100 nucleotides in length. In certain embodiments, the nucleic acids are 10 to 75 nucleotides in length; or 10 to 50 nucleotides; or 10 to 40 nucleotides in length.

Alternatively, the reversible binding pair can be biotin and avidin or biotin and streptavidin, or analogs thereof (i.e. biotin or avidin/streptavidin molecules that have been modified but yet allow for reversible binding as described herein). In another example, the specific binding pair can be an antigen and an antibody. Suitable antigens include, but are not limited to, fluorescein, biotin, digoxigenin, or dinitrophenol. In a further example, the specific binding pair can also be an aptamer and its target molecule. Aptamers can be short nucleic acid or short peptides (e.g., 6-40 kDa) which strongly bind a target molecule, typically with binding constants ($K_d$) in the micromolar to picomolar range (i.e., <1000 µM to <1000 pM). Aptamer targets can include, but are not limited to, an organic dye (e.g., fluorescein, Cy3, Cy5), a disaccharide (e.g., cellobiose, lactose, maltose, gentiobiose), an aminoglycoside (e.g., tobramycin, lividomycin, kanamycin A, kanamycin B, neomycin B), an antibiotic (e.g, viomycin and tetracyclin), dopamine, porphyrins (e.g., hematoporphyrin), and biotin.

In typical embodiments, the first and second compounds include a polypeptide and a molecule as described herein.

As used herein, the term "polypeptide" (used interchangeably with "protein" with the understanding that "polypeptide" is broader in scope) includes a molecule having a sequence of amino acids linked by peptide bonds. This term includes proteins, fusion proteins, oligopeptides, cyclic peptides, and polypeptide derivatives. The protein can include antibodies, enzymes, ligand receptors, and any other type of polypeptides having functional characteristics. The polypeptide can be in its natural conformation or have an altered conformation. It is typically a polymer of at least three amino acids, linked to one another by peptide bonds. In some embodiments, the term is used to refer to specific functional classes of polypeptides, such as, for example, receptors, enzymes, signaling proteins, structural proteins, autoantigen polypeptides, nicotinic acetylcholine receptor polypeptides, alloantigen polypeptides, etc. For each such class, there are several examples of amino acid sequences of known exemplary polypeptides within the class; in some embodiments, such known polypeptides are reference polypeptides for the class. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer, or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

A polypeptide may have from about 10 to about 1000 amino acid residues and, even more typically from about 20 to about 500 amino residues. Thus, as used herein, a polypeptide includes what is often referred to in the art as an oligopeptide (5-10 amino acid residues), a polypeptide (11-100 amino acid residues) and a protein (>100 amino acid residues). A polypeptide encoded by an encoding region can undergo post-translational modification to form conjugates with carbohydrates, lipids, nucleic acids and the like to form glycopolypeptides (e.g., glycoproteins), lipopolypeptides (e.g. lipoproteins) and other like conjugates.

Examples of polypeptides include insulin for the treatment of diabetes, interferon for treating viral infections, interleukins for modulating the immune system, erythropoietin for stimulating red blood cell formation, and growth factors that act to mediate both prenatal and postnatal growth. Carrier polypeptides include β-galactosidase, glutathione-S-transferase, the N-terminus of L-ribulokinase, bacteriophage T4 gp55 protein, and bacterial ketosterioid isomerase protein. An example includes α1-acid glycoprotein (AGP).

As used herein, the term "molecule" includes, for example, any compounds/molecules, wherein the molecular weight of the molecule is less than the molecular weight of the polypeptide. Some typical embodiments include molecules with less than about 1 kDa and polypeptides having less than about 100 kDa and, more specifically, from about 5 kDa to about 100 kDa. In embodiments, the molecule has a diffusion coefficient that is greater than that of the polypeptide. In some embodiments, the diffusion coefficient of the molecule is at least about 2× greater than that of the polypeptide, which also correlates to the molecule having a molecular weight that is at least about 8× lower than the molecular weight of the polypeptide. In other embodiments, the diffusion coefficient of the molecule is at least about 5× greater than that of the polypeptide. In further embodiments, the diffusion coefficient of the molecule is at least about 8× greater than that of the polypeptide. In some embodiments, the molecule can be an enzyme substrate, a ligand, an antagonist, and any other applicable reactant that can bind to a polypeptide. In some embodiments, the molecule is a therapeutic agent. In some embodiments, the molecule is a therapeutic candidate.

The molecule may be a basic, acidic and/or neutral drug. Examples include alpha-blockers, such as Nicergoline or Prazosin; anesthetics/analgesics, such as Alfentanil, Ketamine or Ethidocaine; analgetics, such as Fentanil, Meperidine, Methadone or Phenylbutazone; anesthetics, such as Bupivacaine, Etidocaine or Phencyclidine; anesthetics/antiarrhytmics, such as Lidocaine or Phencyclidin; antiarrhytmics, such as Aprindine, Disopyramide, Quinidine or Verapamil; antibiotics, such as Erythromycin; anticoagulants, such as Acenocoumarol, Dipyridamole, PCR2362 (thienopyridine derivative), Ticlopidine or Warfarin; antiepileptics, such as Phenytoin or Carbamazepine; antiinflammatory agents, such as Naproxen; beta-blockers, such as Alprenolol, Metoprolol, Oxprenolol, Pindolol and related compounds, Propranolol or Timolol; steroids, such as Progesterone, Cortexone, Cortisol, Testosteron, Estradiol or Prednisolone; neuromuscular blockers, such as Metocurine or d-Tubocurarine; psychotropics, such as Amitriptyline, Chlorpromazine, Cyclazindol, Desmethylimipramine, Diazepam, Doxepine, Flurazepam, Fluphenazine, Haloperidol, Imipramine, Loxapine, Mianserin, Nortriptyline, Norzimelidine, Perazine, Perphenazine, Phenobarbital, Phenothiazine derivatives, Promazine, Acepromazine, Protipendyl, Thioridazine, Thiothixene, Triazolam, Trifluoperazine or Zimelidine; vitamins and provitamins, such as Vitamin $B_{12}$ or folic acid; further drugs, such as Aminopyrine, Amoxapine, Bupropion, Maprolitine, Nomifensine, Trazodone, drugs with quaternary ammonium group, Ritodrine, Doxazosin, Trimazosin, Binedalin, Amsacrine, Apazone, SKF 525A, Ciclazindol, PCR 2362, Indomethacin, Probenecid, Retinoic Acid, Sulfinpyrazone, Tolmetin, Benoxaprofen, Heparin, Sufentanil, Lofentanil, Metoclopramide, Nicardipine, Pirmenol, mifepristone, RU 42 633, Aprindil, Auramine O, Bepridil, Desipramine, Desmethylclomipraine, Moxaprindine, Quinine, Lorcainide, Prothipendyl, Protriptyline, Trihexyphenidyl, Biperiden, Methaqualone, Diphenhydramine, Glutethimide, Chlordiazepoxid, L-Tryptophane, Mepivacaine, Levomethadone, Opipramol, Trifluopromazine or Trimipramine; plasticicers, such as tris-butoxyethyl phosphate (TBEP); staurosporine or staurosporine derivatives, such as N-benzoyl-staurosporine or 7-hydroxy staurosporine, as well as a metabolite of any of these compounds; pharmaceutically acceptable salt thereof.

Longitudinal separation by transverse diffusion in laminar pipe flow (LSTDLPF) to determine the equilibrium dissociation constant of a reversible binding pair between a first compound and a second compound such as, without being limited thereto, a polypeptide and a molecule, is described herein. In particular, a mathematical model and its use to simulate the use of LSTDLPF to determine the equilibrium dissociation constant are described in embodiments. Furthermore, the results of a simulation are provided by measuring the equilibrium dissociation constant of reversible binding between a first compound and a second compound. For ease of description, the reversible binding pair is described herein using polypeptides (P) and molecules (SM) but it is understood that it can be applied to any reversible binding pair as defined above in the definition of the term.

In embodiments, a non-calorimetric approach for finding $K_d$ of polypeptide-molecule binding is described in methods and systems, which involves at least one of no labeling, no immobilization, and no inside-the-instrument equilibration.

In an embodiment, longitudinal separation by transverse diffusion in laminar pipe flow (LSTDLPF) was used to determine the equilibrium dissociation constant of a reversible binding pair, both theoretically and experimentally. In a certain embodiment, an equilibrium mixture comprising a polypeptide, a molecule, and molecule-polypeptide complex are injected into a capillary tube. After injection, the equilibrium mixture flows into the capillary tube under laminar flow conditions. The polypeptide and the molecule-polypeptide complex are then separated from the molecule in the longitudinal direction, by different rates of transverse diffusion caused by different diffusion coefficients of the complex and the molecule. A signal proportional to the concentration of the molecule, both unbound and bound to the polypeptide, is measured as a function of time and the equilibrium dissociation constant is determined based on this measured dependence of the signal on time.

In another embodiment, an equilibrium mixture (EM) including P, SM, and P-SM is prepared outside the instrument, and sampled into the instrument for analysis. P-SM and SM are first physically separated based on their diffusion coefficient difference. Separation may be as short as a few seconds to ensure that complex dissociation can be neglected for biologically-relevant complexes, which may have lifetimes as short as a minute (Huber, W. & Mueller, F. *Current Pharmaceutical Design* 2006, 12, 3999-4021 and Nunez, S., Venhorst, J. & Kruse, C. G. *Drug Discovery Today* 2012, 17, 10-22). Finally, a signal from SM (both free and bound) is measured with an on-line detection method; the measured signal is used to provide a binding isotherm from which the value of $K_d$ is determined.

In another embodiment, there is provided a method for determining an equilibrium dissociation constant ($K_d$) of a reversible binding pair of a first compound and a second compound, the method comprising: injecting a sample into a capillary tube via one or more valves, wherein the sample comprises the first compound, the second compound, and a first compound-second compound complex; injecting a mobile phase into the capillary tube via said one or more valves, the sample flowing through the capillary tube under laminar flow conditions, wherein the second compound and the first compound-second compound complex is separated from the first compound by transverse diffusion; measuring time dependence of a signal that is proportional to the concentration of the first compound, both unbound and bound to the second compound using a measurement component; and determining the equilibrium dissociation constant based on the measured signal versus time dependence.

In another embodiment, the method for determining an equilibrium dissociation constant ($K_d$) of a reversible binding pair of a polypeptide and a molecule comprises: injecting, into a capillary tube having an inlet and an outlet, an equilibrium mixture comprising the polypeptide, the molecule, and molecule-polypeptide complexes at the capillary tube inlet, the equilibrium mixture flowing through the capillary tube propelled by a mobile phase pushed forward by pressure under laminar flow conditions; separating the polypeptide, and the molecule-polypeptide complexes, from the molecule by transverse diffusion; measuring, using a measurement component, time dependence of a signal that is proportional to the concentration of the molecule, both unbound and bound to the polypeptide; and determining the equilibrium dissociation constant based on the measured signal versus time dependence.

In some embodiments of the method, the diffusion coefficient of the molecule is at least about 2× greater than that of the polypeptide. In other embodiments of the method, the molecule has a diffusion coefficient that is at least about 5× greater than that of the polypeptide. In still other embodiments of the methods, the molecule has a diffusion coefficient that is at least about 8× greater than that of the polypeptide.

In some embodiments of the method, injecting the equilibrium mixture comprises injecting the equilibrium mixture at a flow rate less than or about Q/10 to, typically obtain approximately a cylindrical plug shape; injecting a plug of a buffer at a flow rate less than or about Q/10 to displace the cylindrical plug from the capillary's inlet at a distance much greater than the capillary's diameter; and propagating the equilibrium mixture under laminar flow conditions at a flow rate of $Q=\pi LD_{SM}$, wherein Q is the flow rate, L is the capillary tube's length, and $D_{SM}$ is the diffusion coefficient of the molecule.

In some embodiments of the method, the injection is controlled by one or more valves. In some embodiments, the one or more valves are controlled by one or more controllers. In other embodiments, the one or more valves are controlled by a central controller. In further embodiments, the one or more controllers or the central controller execute software instructions to instruct the valves to perform the injection described herein.

In some embodiments of the method, the capillary tube has a tube length L that is proportional to a flow rate Q under the laminar flow conditions, wherein the proportion is determined by the formula $Q=\pi LD_{SM}$, where $D_{SM}$ is the diffusion coefficient of the molecule. In some embodiments of the method, the diffusion coefficient of the molecule is from about 100 μm²/s to about 1000 μm²/s and more typically, from about 500 μm²/s to about 700 μm²/s. In certain embodiments, the diffusion coefficient of the molecule is about 500 μm²/s.

In embodiments for the range of Q, L can have a range from about 1 cm to about 300 cm, and the diffusion coefficient of SM from about 100 μm²/s to about 1000 μm²/s. The flow rate can be from about 0.2 μL/min to about 600 μL/min, more typically, about 50 μL/min to about 400 μL/min, about 50 μL/min to about 200 μL/min, or about 50 μL/min to about 100 μL/min. In some embodiments of the method, the laminar flow conditions are realized at a flow rate of about 50 μL/min. In some embodiments of the method, the laminar flow conditions are realized at a flow rate of from about 50 μL/min to about 100 μL/min. In some embodiments of the method, the laminar flow conditions are maintained by pressure injection of the mobile phase into the capillary tube.

In some embodiments of the method, the capillary tube has a diameter d greater than $\rho LD_{SM}/(500\eta)$ when Reynolds number is less than about 2000, wherein $\rho$ and $\eta$ are the density and dynamic viscosity of the mobile phase injected into the capillary tube to maintain laminar flow conditions, respectively.

In some embodiments of the method, the mobile phase is a buffer. The buffer may include about 30 mM ammonium acetate buffer at about pH 7.5. In some embodiments of the method, the buffer has a density of about $10^3$ kg·m⁻³. In some embodiments of the method, the buffer has a dynamic viscosity of about $8.9 \times 10^{-4}$ Pa·s.

In some embodiments of the method, the separation time $t_{sep}$ of the unbound molecules and the molecules bound to the polypeptide can be found by using the formula $t_{sep}=d^2/(4D_{SM})$ wherein d is the diameter of the capillary tube and the $D_{SM}$ is the diffusion coefficient of the molecule. In some embodiments of the method, the separation time correlates with transverse diffusion of SM (across the capillary radius). As seen from the formula, it can depend on d and $D_{SM}$. In certain embodiments, the value of d may vary from about 10 to about 300 μm, while $D_{SM}$ may vary from about 100 to about 1000 μm²/s, and accordingly, $t_{sep}$ can vary from about 0.025 to about 225 s. In certain embodiments, the separation time is about 20 s. In some embodiments of the method, the separation time is from about 0.2 to about 20 s.

In certain embodiments of the methods and system for determining an equilibrium dissociation constant ($K_d$) of a reversible binding pair described herein, the advantages include faster elution and separation with minimum (e.g. low to no) adsorption of the reversible binding pair of polypeptide and molecule on the inner wall of the capillary tube.

In fluid dynamics, laminar flow occurs when a fluid flows in parallel layers, with no disruption between the layers. In laminar flow, the motion of the particles of the fluid is very orderly with particles close to a solid surface moving in straight lines parallel to that surface. When a fluid is flowing through a closed channel such as a pipe or between two flat plates, either of two types of flow may occur depending on the velocity and viscosity of the fluid: laminar flow or turbulent flow. Laminar flow tends to occur at lower velocities. At low velocities, the fluid tends to flow without lateral mixing. Unlike turbulent flow, in laminar flow there are no cross-currents perpendicular to the direction of flow, nor eddies or swirls of fluids. Laminar flow is known to be a flow regime typically characterized by high-momentum diffusion, low-momentum convection, and pressure and velocity independence from time. The (dimensionless) Reynolds number characterizes whether flow conditions lead to laminar or turbulent flow. The Reynolds number is the ratio of the inertial force to the shearing force of the fluid: how fast the fluid is moving relative to how viscous it is, irrespective of the scale of the fluid system. Laminar flow generally occurs when the fluid is moving slowly or the fluid is very viscous. As the Reynolds number increases, such as by increasing the flow rate of the fluid, the flow will transition from laminar to turbulent flow at a specific range of Reynolds numbers, the laminar-turbulent transition range depending on small disturbance levels in the fluid or imperfections in the flow system. Generally, laminar flow can be achieved by modulating one or more of the following conditions: transverse dimension of the flow (e.g., inner diameter of the capillary), pressure, temperature, and viscosity. Typically, it is difficult to create turbulent flow inside a capillary tube; thus, a person skilled in the art can readily obtain the conditions to ensure laminar flow inside the capillary.

In some embodiments, to maintain laminar flow conditions, the mobile phase is injected continuously under constant pressure. In some embodiments, the high-pressure pump used to inject the mobile phase is a high-pressure liquid chromatography (HPLC) system. In other embodiments, the mobile phase is injected at a propagation pressure of about 4 psi (i.e., about 41 μL/min). In certain embodiments, the pressure is selected to achieve a flow rate of about 0.2 to about 600 μL/min, more typically, about 50 μL/min to about 400 μL/min, about 50 μL/min to about 200 μL/min, or about 50 μL/min to about 100 μL/min.

In some embodiments, once the molecule-polypeptide, the polypeptide, and the molecule have been separated by transverse diffusion, a signal proportional to each of the molecules bound or unbound to the polypeptide are measured. In some embodiments of the method, the signals are measured near the capillary tube outlet. In other embodiments, the signals are measured at the outlet of the capillary tube.

The signals can be measured by using a variety of techniques and methods known to a person skilled in the art. In some embodiments of the method, the signals are measured using mass spectrometry. In further embodiments, the mass spectrometry comprises atmospheric pressure chemical ionization (APCI) mass spectrometry. In some embodiments of the method, where mass spectrometry is used to measure the signals corresponding to the concentrations of the bound and unbound molecules, the method further comprises compensating for the polypeptide's effect on the signals measured for the molecule. In some embodiments of the method, screening of the signal of the molecule by the polypeptide is compensated for.

In some embodiments of the method, the signals are measured using optical spectroscopy. In further embodiments, the optical spectroscopy comprises fluorescence spectroscopy. In some embodiments of the method, optical spectroscopy is used to measure the signals corresponding to the concentrations of the bound and unbound molecules. One skilled in the art would understand how to choose a suitable mobile phase depending on the detector used. For example, if the detector is a mass spectrometer, the mobile phase typically has a lower salt concentration. In more typical embodiments with a mass spectrometer, the mobile phase is volatile (e.g. acetate-, carbonate and/or formate-based buffers). In other embodiments, if the detector is an optical detector, such as a light-absorbance spectrometer or a fluorescence spectrometer, the mobile phase would be selected to have suitable characteristics for absorbance and/or fluorescence measurements, such as a transparent mobile phase. It is understood that with increasing viscosity of the mobile phase, the diffusion will slow and separation time will increase. In addition, in embodiments, the mobile phase is selected to be similar to the physiological environment that SM would be used in (e.g. cell surface, external to the cell, etc.) without compromising the detection of SM. Typically, the mobile phase is a buffer (e.g. pH buffer).

As used herein, the term "mobile phase" (or an eluent) is selected such that it allows the sample of the first and second compounds, and the reverse binding pair (e.g. polypeptides, molecules, and polypeptide-molecule complexes) to elute from the capillary so that the $K_d$ may be measured. The sample itself may be prepared from the mobile phase or any other suitable fluid.

In some embodiments, upon determination of the time dependence of signals that are proportional to the concentration of the bound and unbound molecule, the equilibrium dissociation constant of a reversible binding pair of the polypeptide and the molecule can be determined. In some embodiments of the method, the dissociation constant ($K_d$) is determined by non-linear regression of a binding isotherm with the following equation (equation 5 as described in the Examples below):

$$R = \frac{[SM]_{eq}}{[SM]_0} = \frac{([SM]_0 - [P]_0 - K_d) + \sqrt{([SM]_0 - [P]_0 - K_d)^2 + 4K_d[SM]_0}}{2[SM]_0}$$

wherein:

R is the ratio of concentration of free molecule compared to the total concentration of molecule in the equilibrium mixture;

$[P]_0$ is the total polypeptide concentration in the equilibrium mixture;

$[SM]_{eq}$ is the equilibrium concentration of the molecule in the equilibrium mixture; and $[SM]_0$ is the total concentration of the molecule in the equilibrium mixture.

In one embodiment, there is provided a system for determining an equilibrium dissociation constant ($K_d$) of a reversible binding pair of a first compound and a second compound, comprising: a capillary tube; a sample injector configured for injecting a sample into the capillary tube, the sample comprising the first compound, the second compound, and the first compound-the second compound complex; a mobile phase injector configured for injecting a mobile phase into the capillary tube; one or more valves controlling the sample injector and the mobile phase injector, the one or more valves configured to allow injection of the sample under laminar flow conditions within the capillary tube and separation of the second compound and the first compound-second compound complex from the first compound by transverse diffusion within the capillary tube; and a measurement component configured for measuring time dependence of the signal that is proportional to the concentration of the first compound, both unbound and bound to the second compound.

In one embodiment, a system for determining the equilibrium dissociation constant ($K_d$) of a reversible binding pair of a polypeptide and a molecule includes a capillary tube having an inlet and an outlet; a mixture injector configured for injecting an equilibrium mixture into the capillary tube at the inlet, the equilibrium mixture comprising the polypeptide, the molecule, and molecule-polypeptide complexes; a mobile phase injector configured for injecting a mobile phase into the capillary tube at the inlet; one or more valves controlling the mixture injector and the mobile phase injector, the one or more valves configured to allow injection of the equilibrium mixture under laminar flow conditions within the capillary tube and separation of the polypeptide and the molecule-polypeptide complexes from the molecule by transverse diffusion within the capillary tube; and a measurement component configured for measuring time dependence of the signal that is proportional to the concentration of the molecule, both unbound and bound to the polypeptide.

In some embodiments of the system, the controller operating one or more valves is a processor. In some embodiments of the system, the processor is included in a computing device, such as a desktop computer, laptop, mobile device, and the like.

In some embodiments of the system, the measurement component comprises a mass spectrometer. In further embodiments, the mass spectrometer comprises an atmospheric pressure chemical ionization (APCI) mass spectrometer. In some embodiments, the mass spectrometer is a QTRAP 6500+ time-of-flight (Q-TOF) instrument (Sciex, Concord, ON, Canada) with a commercial Turbo V APCI ionization source. In some embodiments of the system, a controller can be programmed to compensate for the polypeptide's effect on the signal measured for the molecule. In some embodiments of the system, screening by the polypeptide is compensated for.

In some embodiments, the measurement component comprises an optical spectrometer. In further embodiments, the optical spectrometer comprises a fluorescence spectrometer. In some embodiments of the system, a controller can be programmed to compensate for the polypeptide's effect on the signal measured for the molecule.

In some embodiments, a controller is programmed to instruct the one or more valves in the following sequence: allow sample injector to inject the sample at a flow rate less than or about Q/10 to typically, obtain a uniform plug shape (e.g. approximately a cylindrical plug shape or any shape that allows uniform application of the plug to the capillary); allow the mobile phase injector to inject a plug of the mobile phase at a flow rate less than or about Q/10 to displace the plug without substantially affecting the plug shape and displacing the cylindrical plug from the capillary's inlet at a distance greater than the capillary's diameter; and allow the mobile phase injector to propagate the equilibrium mixture under laminar flow conditions at flow rate $Q=\pi LD_{SM}$ wherein Q is the flow rate, L is the capillary tube's length, and $D_{SM}$ is the diffusion coefficient of the molecule.

In some embodiments, a controller is programmed to instruct the one or more valves in the following sequence: allow sample injector to inject the sample at a flow rate less than or about Q/10 to typically, obtain a uniform plug shape (e.g. approximately a cylindrical plug shape); allow the mobile phase injector to inject a plug of the mobile phase at a flow rate less than or about Q/10 to displace the plug without substantially affecting the plug shape; allow the mobile phase injector to inject a plug of the mobile phase at a flow rate less than or about Q/10 to displace the cylindrical plug from the capillary's inlet at a distance greater than the capillary's diameter; and allow the mobile phase injector to propagate the equilibrium mixture under laminar flow conditions at flow rate $Q=\pi LD_{SM}$ wherein Q is the flow rate, L is the capillary tube's length, and $D_{SM}$ is the diffusion coefficient of the molecule.

In some embodiments of the system, the diffusion coefficient of the molecule utilized is at least about 2× greater than that of the polypeptide. In other embodiments of the system, the molecule utilized has a diffusion coefficient that is at least about 5× greater than that of the polypeptide. In still other embodiments of the system, the molecule has a diffusion coefficient that is at least about 8× greater than that of the polypeptide.

In some embodiments of the system, the injection is controlled by one or more valves. In some embodiments of the system, the one or more valves are controlled by one or more controllers. In some embodiments of the system, the one or more valves are controlled by a central controller. In some embodiments of the system, the one or more controllers or the central controller executes software instructions to instruct the valves to perform the injection described herein.

In some embodiments of the system, the capillary tube has a tube length L that is proportional to a flow rate Q under the laminar flow conditions, wherein the proportion is determined by the formula $Q=\pi LD_{SM}$, where $D_{SM}$ is the diffusion coefficient of the molecule. In some embodiments of the system, the diffusion coefficient of the molecule is from about 100 $\mu m^2/s$ to about 1000 $\mu m^2/s$ and more typically, from about 500 $\mu m^2/s$ to about 700 $\mu m^2/s$. In certain embodiments, the diffusion coefficient of the molecule is about 500 $\mu m^2/s$.

In embodiments for the range of Q, L can have a range from about 1 cm to about 300 cm, and the diffusion coefficient of SM from about 100 $\mu m^2/s$ to about 1000 $\mu m^2/s$. The flow rate can be from about 0.2 µL/min to about 600 µL/min, more typically, about 50 µL/min to about 400 µL/min, about 50 µL/min to about 200 µL/min, or about 50 µL/min to about 100 µL/min. In some embodiments of the system, the laminar flow conditions are realized at a flow rate of about 50 µL/min. In some embodiments of the system, the laminar flow conditions are realized at a flow rate of from about 50 µL/min to about 100 µL/min. In some embodiments of the system, the laminar flow conditions are maintained by pressure injection of the mobile phase into the capillary tube.

In some embodiments of the system, the mobile phase is injected continuously into the capillary tube to maintain laminar flow conditions. In some embodiments of the system, the system comprises a high-pressure liquid chromatography (HPLC) system configured to inject the mobile phase. In some embodiments of the system, the mobile phase is injected at a propagation pressure of about 4 psi (which corresponds to flow rate of about 41 µL/min). In certain embodiments, the pressure is selected to achieve a flow rate of about 0.2 to about 600 µL/min, more typically, about 50 µL/min to about 400 µL/min, about 50 µL/min to about 200 µL/min, or about 50 µL/min to about 100 µL/min.

In some embodiments of the system, the mobile phase is a buffer. The buffer may include 30 mM ammonium acetate buffer at pH 7.5. In some embodiments of the system, the buffer has a density of $10^3$ kg·m$^{-3}$. In others, the buffer has a dynamic viscosity of $8.9 \times 10^{-4}$ Pa·s.

In some embodiments of the system, the capillary tube has a diameter d greater than $\rho L D_{SM}/(500\eta)$ when Reynolds number is less than about 2000, wherein $\rho$ and $\eta$ are the density and dynamic viscosity of the mobile phase injected into the capillary tube to maintain laminar flow conditions, respectively.

In some embodiments of the system, the separation time $t_{sep}$ of the unbound molecules and the molecules bound to the polypeptide can be found by using the formula $t_{sep} = d^2/(4D_{SM})$ wherein d is the diameter of the capillary tube and the $D_{SM}$ is the diffusion coefficient of the molecule. In some embodiments of the system, the separation time correlates with transverse diffusion of SM (across the capillary radius). As seen from the formula, it can depend on d and $D_{SM}$. In certain embodiments, the value of d may vary from about 10 to about 300 µm, while $D_{SM}$ may vary from about 100 to about 1000 µm$^2$/s, and accordingly, $t_{sep}$ can vary from about 0.025 to about 225 s. In certain embodiments, the separation time is about 20 s. In some embodiments of the system, the separation time is from about 0.2 to about 20 s.

In some embodiments of the system, the dissociation constant ($K_d$) is determined by non-linear regression of a binding isotherm with the following equation (equation 5 as described in the Examples below):

$$R = \frac{[SM]_{eq}}{[SM]_0} = \frac{([SM]_0 - [P]_0 - K_d) + \sqrt{([SM]_0 - [P]_0 - K_d)^2 + 4K_d[SM]_0}}{2[SM]_0}$$

wherein:

R is the ratio of concentration of free molecule compared to the total concentration of molecule in the equilibrium mixture;

$[P]_0$ is the total polypeptide concentration in the equilibrium mixture;

$[SM]_{eq}$ is the equilibrium concentration of the molecule in the equilibrium mixture; and $[SM]_0$ is the total concentration of the molecule in the equilibrium mixture.

In some embodiments, the methods and systems described herein are label-free and immobilization-free and allow that $K_d$ measurements of the equilibrium dissociation constant of reversible binding pair of polypeptide-molecule complexes. Embodiments of the methods can be implemented using components, such as void capillaries and high-pressure liquid chromatography (HPLC) pump.

As seen in the Examples disclosed herein, the methods and systems may provide repeatability and reproducibility and demonstrate accuracy. In some embodiments, as the mixture is equilibrated prior to the propagation stage, the method is independent of the association rate of the reaction. In some embodiments, when LSTDLPF-based methods are coupled with mass-spectrometry (MS) detection, amounts and concentrations of samples can be reduced, for measuring very low $K_d$. In some embodiments, the screening effect generated by the free polypeptide in the ionization source was taken into account and a compensation procedure was utilized to determine an accurate $K_d$. Accordingly, the methods may become a solution-based tool for the screening of polypeptide-molecule complexes.

Other methodologies for $K_d$ determination based on the difference in the diffusion coefficients of SM and P and utilizing a capillary tube have also been developed (H. Jensen, J. Østergaard, *J. Am. Chem. Soc.* 2010, 132, 4070-4071, N. N. Poulsen, N. Z. Andersen, J. Østergaard, G. Zhuang, N. J. Petersen, H. Jensen, *Analyst* 2015, 140, 4365-4369, S. M. Clark, L. Konermann, *J. Am. Soc. Mass. Spectrom.* 2003, 14, 430-441, and S. M. Clark, L. Konermann, *Anal. Chem.* 2004, 76, 7077-7083). In the case of other methodologies, the equilibrium mixture is injected by pressure in a plug (H. Jensen, J. Østergaard, *J. Am. Chem. Soc.* 2010, 132, 4070-4071, N. N. Poulsen, N. Z. Andersen, J. Østergaard, G. Zhuang, N. J. Petersen, H. Jensen, *Analyst* 2015, 140, 4365-4369), or in a continuous mode (S. M. Clark, L. Konermann, *Anal. Chem.* 2004, 76, 7077-7083), and is propagated hydrodynamically until the detection point, to yield either a Gaussian-peak or a front followed by a plateau, respectively. The experimental signal is then used to perform a non-linear regression through which $K_d$ can be determined. Nevertheless, these approaches differ from the methods and systems as described herein by the fact that these approaches do not use any separation between the species in the longitudinal direction, but, on the contrary, utilize long propagation times (usually ~10 min) and fast mixing (Holyst, R. *Anal. Chim. Acta* 2015, 855, 51-59) to allow each species to have time to diffuse several times through the capillary cross section. These longer times of propagation and fast mixing allow enough time for P and P-SM to adsorb onto the capillary walls, therefore introducing errors in the determination of $K_d$. These methods also use a longer capillary tube (usually about 3 m), and large volumes, and accordingly, amounts of the polypeptide. Accordingly, the methods and systems as described herein may have faster propagation, therefore there is less adsorption of P and P-SM onto the inner wall of the capillary tube, which can improve the accuracy and facilitate faster screening.

Furthermore, in some embodiments of the LSTDLPF based methods and systems, these are not dependent on separation that is based on the pH, the ionic strength, or the composition of the mobile phase. Also, in some embodiments of the methods and systems as described herein the use of any stationary phase such as a sieving matrix, gel or coating is not required; since differential transverse diffusion of species in an unfilled capillary tube can provide the separation in the longitudinal direction.

Finally, in some embodiments, automated systems using or otherwise incorporating the methods and systems as described herein can allow rapid examination (or ranking) of different molecules, for example, as potential therapeutic agents.

The following Examples, set forth to aid in the understanding of the invention, and should not be construed to limit in any way the scope of the invention as defined in the claims which follow thereafter.

EXAMPLES

Example 1—LSTDLPF Separation Time Scale

Whether or not LSTDLPF could provide separation of P, SM, and P-SM in a sub-minute time scale was evaluated. In some embodiments, SM, with a diffusion coefficient of $D_{SM}$, diffuses in transverse direction on a distance equal to the capillary tube's inner radius, i.e., d/2 where d is the capillary tube's inner diameter. Therefore, the separation time, $t_{sep}$, is defined by the characteristic diffusion time of SM over distance d/2, which, in turn, equals $d^2/4D_{SM}$ (V. Okhonin, E. Wong, S. N. Krylov, *Anal. Chem.* 2008, 80, 7482-7486). Therefore, the separation time is equal to:

$$t_{sep} = d^2/(4D_{SM}) \quad (3)$$

Due to stronger dependence of $t_{sep}$ on d than on $D_{SM}$ and due to a larger range of possible d than $D_{SM}$, $t_{sep}$ is mainly defined by the value of d. For a typical $D_{SM}$ of $5\times10^2$ μm²/s in water (F. Ye, H. Jensen, S. W. Larsen, A. Yaghmur, C. Larsen, J. Østergaard, *J. Pharm. Biomed. Anal.* 2012, 61, 176-183), and d ranging from 20 to 200 μm, $t_{sep}$ ranges from 0.2 to 20 s. Thus, LSTDLPF allows separation to occur within a sub-minute time scale.

Example 2—In Silico Study—Accuracy of $K_d$

In this example, it was evaluated whether or not LSTDLPF separation of P-SM from SM could theoretically facilitate accurate determination of $K_d$. LSTDLPF is based on 3 key processes: longitudinal advection of SM, P, and P-SM in LPF, their transverse diffusion (longitudinal diffusion can be neglected) (V. Okhonin, E. Wong, S. N. Krylov, *Anal. Chem.* 2008, 80, 7482-7486), and their reversible binding. These processes are deterministic in their nature, and, therefore, the spatiotemporal behaviour of [SM], [P], and [P-SM] in LSTDLPF can be accurately modeled by computer simulation.

In this example, a virtual LSTDLPF setup in COMSOL Multiphysics software was created and used to model $K_d$ determination (FIG. 1). The virtual setup simulated an experiment in which: 1) EM is prepared outside the capillary (i); 2) a short plug of EM is injected by pressure into the capillary pre-filled with a buffer; 3) EM at the capillary inlet is displaced by the buffer; 4) the buffer is continuously pressure-injected into the capillary to create LPF and separate SM from P-SM and P; and 5) concentrations of SM, P, and P-SM (averaged through the capillary cross-section) are recorded at the capillary end as functions of time. The shapes of EM, SM, P and P-SM inside the capillary during the different simulations stages are shown in FIG. 1A: (ii) Initially when EM is injected at the capillary inlet and at a later time (iii) when SM is separated from P and P-SM during the continuous pressure injection stage. As illustrated in FIG. 1A, the profiles of P and P-SM are similar due to similarity of their sizes, and, thus, diffusion coefficients. The parameters (diffusion coefficients, rate constants, concentrations, flow rates, and capillary dimensions) are chosen in the ranges reasonable from an experimental standpoint.

In order to study the feasibility to extract $K_d$ by LSTDLPF-based methods, simulations were computed. To simulate temporal propagation patterns (time dependencies of [SM], [P], and [P-SM] at the capillary end), in the COMSOL software, the following set of partial differential equations was utilized to describe the longitudinal advection, the diffusion, and the reaction processes involved during the propagation:

$$\frac{\partial [P]}{\partial t} + v(r)\frac{\partial [P]}{\partial x} - D_P\left(\frac{\partial^2 [P]}{\partial^2 x} + \frac{1}{r}\frac{\partial}{\partial r}\left(r\frac{\partial [P]}{\partial r}\right)\right) =$$

-continued $$-k_{on}[P][SM] + k_{off}[P-SM]$$

$$\frac{\partial [SM]}{\partial t} + v(r)\frac{\partial [SM]}{\partial x} - D_{SM}\left(\frac{\partial^2 [SM]}{\partial^2 x} + \frac{1}{r}\frac{\partial}{\partial r}\left(r\frac{\partial [SM]}{\partial r}\right)\right) =$$

$$-k_{on}[P][SM] + k_{off}[P-SM]$$

$$\frac{\partial [P-SM]}{\partial t} + v(r)\frac{\partial [P-SM]}{\partial x} -$$

$$D_{P-SM}\left(\frac{\partial^2 [P-SM]}{\partial^2 x} + \frac{1}{r}\frac{\partial}{\partial r}\left(r\frac{\partial [P-SM]}{\partial r}\right)\right) =$$

$$k_{on}[P][SM] - k_{off}[P-SM]$$

where D is the diffusion coefficient, r is the radial coordinate, and v(r) is the parabolic velocity profile of LPF described by:

$$v(r) = v_{max}\left(1 - \frac{4r^2}{d^2}\right), \quad v_{max} = 2v_{av}$$

where $v_{max}$ is the velocity in the capillary centre and $v_{av}$ is the average velocity as:

$$v_{av} = \frac{4Q}{\pi d^2}$$

with:

$$Q = Q_{inj} = 5 \ \mu L/min, \ 0 < t < t_2$$

$$Q = Q_{prop} = 50 \ \mu L/min, \ t > t_2$$

The initial conditions are:

[P]=0, [SM]=0, [P-SM]=0; 0≤x≤L, t=0 where L is the length of the capillary.
The boundary conditions are:

[P]=[P]$_{eq}$, [SM]=[SM]$_{eq}$, [P-SM]=[P-SM]$_{eq}$; x=0,
0<t<t$_{inj}$ $D_P\partial_r[P]$=0, $D_{SM}\partial_r[SM]$=0, $D_{P-SM}\partial_r[P-SM]$=0; r=d/2,
0<t<t$_{inj}$ $D_P\partial_x[P]$=0, $D_{SM}\partial_x[SM]$=0, $D_{P-SM}\partial_x[P-SM]$=0; x=L,
0<t<t$_{inj}$ and:

[P]=0, [SM]=0, [P-SM]=0; x=0, t$_{inj}$<t $D_P\partial_r[P]$=0, $D_{SM}\partial_r[SM]$=0, $D_{P-SM}\partial_r[P-SM]$=0; r=d/2,
t$_{inj}$<t $D_P\partial_x[P]$=0, $D_{SM}\partial_x[SM]$=0, $D_{P-SM}\partial_x[P-SM]$=0; x=L,
t$_{inj}$<t Temporal propagation profiles of SM, P, and P-SM (i.e. time dependencies of [SM], [P], and [P-SM] at the capillary end) obtained in a representative simulation are shown in FIG. 1B. The simulation conditions are as follows: internal capillary diameter=200 μm, capillary length=50 cm, flow rate of LPF=50 μL/min, EM injection by 5 μL/min for 12 s, $k_{off}$=10$^{-3}$ s$^{-1}$, $k_{on}$=10$^3$ M$^{-1}$ s$^{-1}$ ($K_d$=$k_{off}$/$k_{on}$=10$^{-6}$ M), $D_{SM}$=500 μm²/s, $D_P$=$D_{P-SM}$=50 μm²/s, [SM]$_0$=5×10$^{-7}$ M, and [P]$_0$=5×10$^{-7}$ M.

As P and P-SM are similar in size, they have similar diffusion coefficients and result in similar bimodal propagation profiles. The first peak corresponds to P and P-SM that were located near the center of the capillary in the beginning of separation and did not have enough time to diffuse to the capillary wall during the propagation. Inversely, the tail corresponds to P and P-SM that were initially located near the wall and did not have time to diffuse to the center. The propagation profile of SM is qualitatively different from those of P and P-SM as it is unimodal. Fast diffusion of SM allows it to re-equilibrate across the capillary during the time of propagation. As a result, SM shows a single peak which is wider than the first peak of P and P-SM but does not tail as long as trails of P and P-SM.

The results of a real experiment were mimicked to determine whether the $K_d$ calculated from these results are equal to those used in simulation. To obtain data sufficient for extracting $K_d$, the total concentration of SM ($[SM]_0=[SM]+[P-SM]$) was fixed and that of P ($[P]_0=[P]+[P-SM]$) in EM was varied (Heegaard, N. H. H & Kennedy, R. T. *Electrophoresis* 1999, 20, 3122-3133).

Figure 1D:
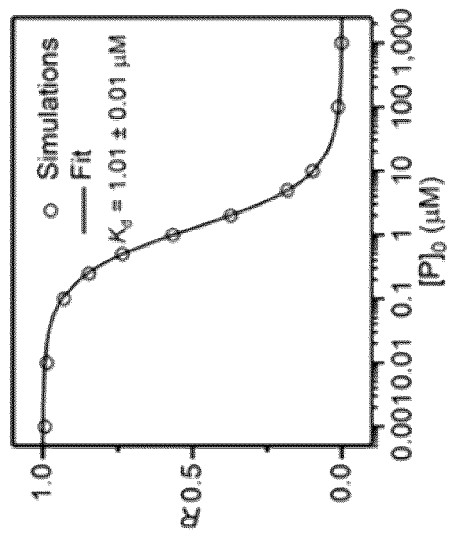
Figure 1A:
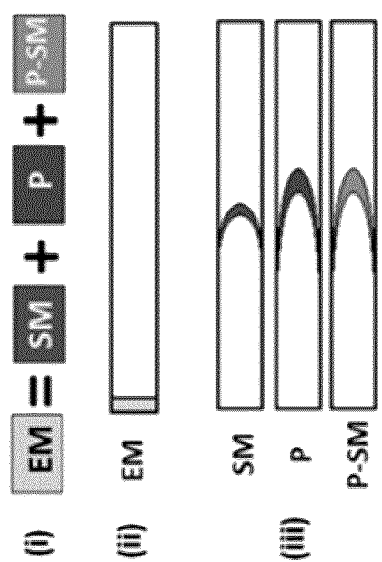
Figure 1C:
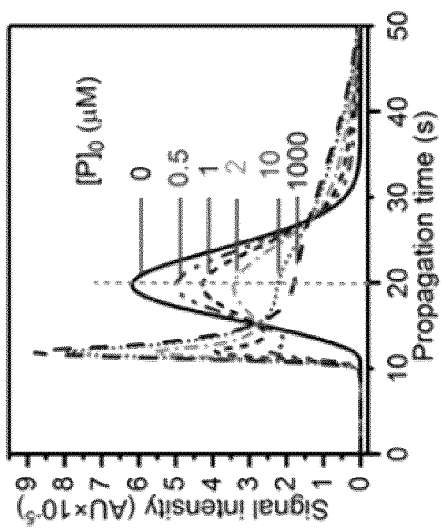
Figure 2B:
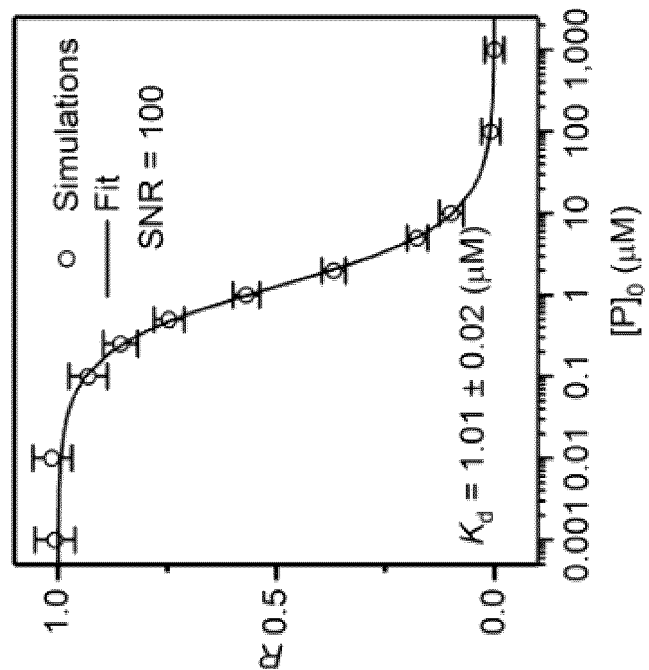
FIGS. 2A and 2B illustrate the effect of random noise (0.01 of signal value) on accuracy of $K_d$ determination by LSTDLPF-based methods according to embodiments.
Figure 2A:
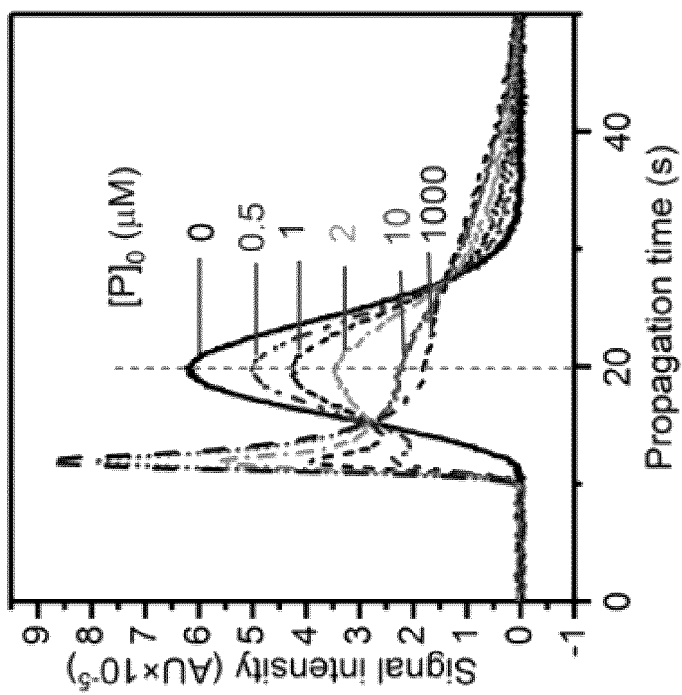
Figure 3B:
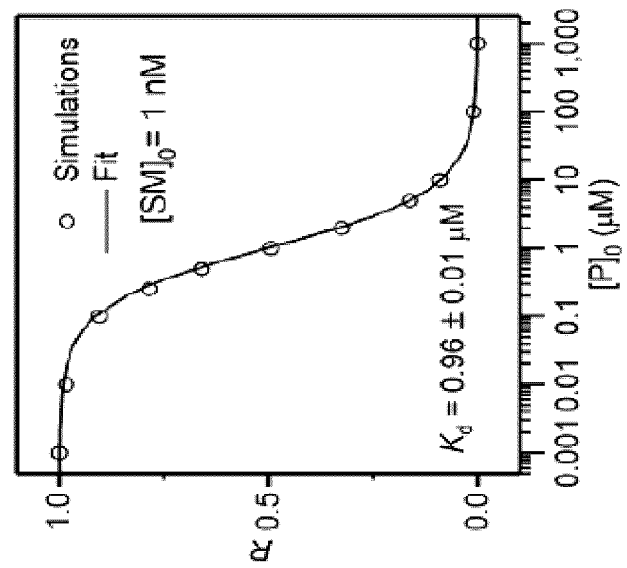
FIGS. 3A and 3B, in comparison with FIG. 1A an 1B, illustrate the effect of variation of $[SM]_0$ ($[SM]_0=0.5$ μM in FIGS. 1A and 1B and $[SM]_0=1$ nM in FIGS. 3A and 3B) on accuracy of $K_d$ determination by LSTDLPF-based methods according to embodiments.
Figure 3A:
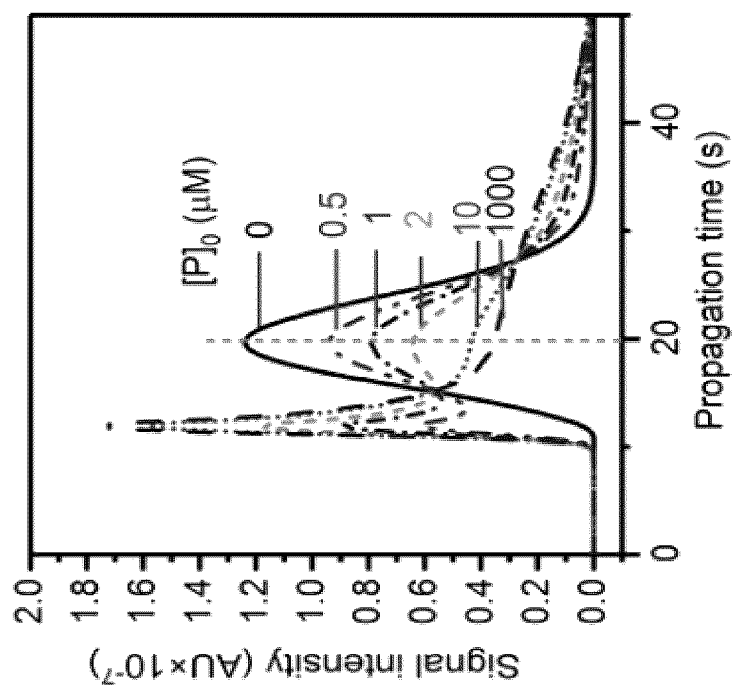
Figure 5A:
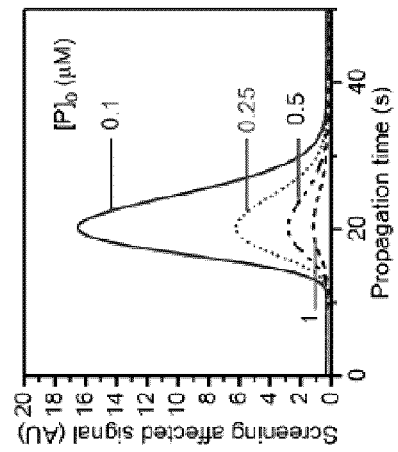
FIGS. 5A and 5B illustrate the effect of a screening effect on accuracy of $K_d$ determination by LSTDLPF-based methods according to an embodiment.
Figure 5B:
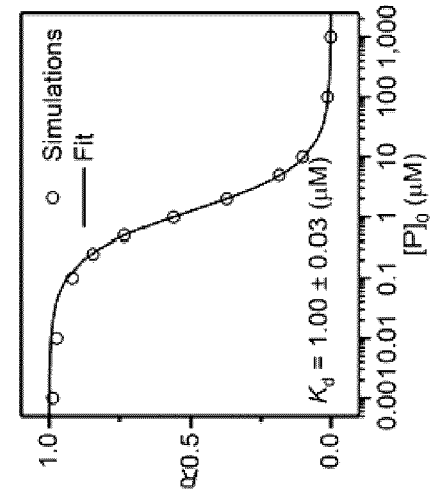
Figure 5C:
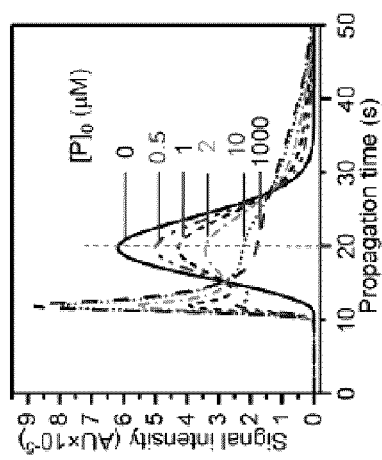
FIG. 5C illustrates the curves obtained after signal compensation procedures.
Figure 5D:
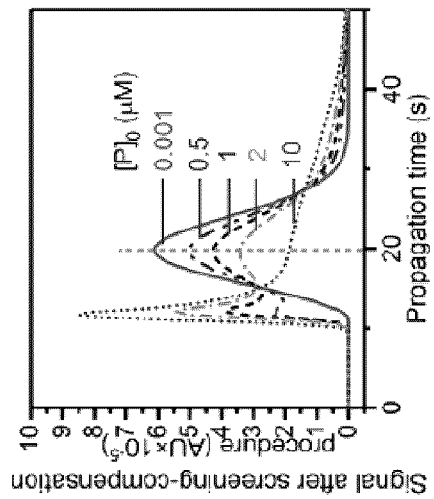
FIG. 5D illustrates a binding isotherm obtained from the data illustrated in FIG. 5C.

To mimic the simplest LSTDLPF experiment, 1) propagation profiles of SM, P, and P-SM were simulated with a constant $[SM]_0$ (smaller than $K_d$) and varying $[P]_0$; and 2) presented the results of simulation as signal (proportional to $[SM]+[P-SM]$) versus time (FIG. 1C). The obtained propagation profiles are bimodal, with the first and second peaks corresponding to P-SM and SM, respectively. The first peak is absent in the absence of P, when the fraction of unbound SM is equal to unity. The second peak is absent if $[P]_0 \gg K_d$, when the fraction R of unbound SM is near zero. In the intermediate cases ($[P]_0 \sim K_d$), both peaks are present. Peak maxima do not shift significantly with the variation of $[P]_0$. The ratio between detection times of second and first peaks equals approximately 2, which corresponds to a 2× difference between the maximum and average velocities of LPF.

Accordingly, the calculated $K_d$ differed from the one used in simulations by about 1%. The small overestimation of $K_d$ may be caused by some dissociation of the polypeptide-molecule complex during LSTDLPF. Computer simulations and the above-described procedure of extracting $K_d$ from the simulated data were then used to confirm robustness of finding $K_d$ with respect to: random noise in signal and change of $[SM]_0$, and the results are illustrated in FIGS. 2A-2B and 3A-3B, respectively. The results gave 1% and 4% of error, respectively, that were considered acceptable. The simulation conditions for assessing the effect of random noise were: internal capillary diameter=200 μm, capillary length=50 cm, flow rate of LPF=50 μL/min, EM injection by 5 μL/min for 12 s, $k_{off}=10^{-3}$ s$^{-1}$, $k_{on}=10^3$ M$^{-1}$ s$^{-1}$ ($K_d=k_{off}/k_{on}=10^{-6}$ M), $D_{SM}=500$ μm$^2$/s, $D_P=D_{P-SM}=50$ μm$^2$/s, $[SM]_0=5\times10^{-7}$ M, and $[P]_0$ ranging from 0 to 1000 μM (see FIG. 2A). The simulation conditions for assessing the effect on change of $[SM]_0$ were: internal capillary diameter=200 μm, capillary length=50 cm, flow rate of LPF=50 μL/min, EM injection by 5 μL/min for 12 s, $k_{off}=10^{-3}$ s$^{-1}$, $k_{on}=10^3$ M$^{-1}$ s$^{-1}$ ($K_d=k_{off}/k_{on}=10^{-6}$ M), $D_{SM}=500$ μm$^2$/s, $D_P=D_{P-SM}=50$ μm$^2$/s, $[SM]_0=10^{-9}$ M, and $[P]_0$ ranging from 0 to 1000 μM (see FIG. 3A).

From a data set obtained in computer simulations and shown in FIG. 1C, a classical binding isotherm may be built: a fraction of unbound SM versus $[P]_0$. A simplifying assumption may be made that the signal is an additive function, i.e., a signal from a mixture of P-SM and SM is equal to a sum of signals from pure P-SM and SM at concentrations similar to those in the mixture. In this case, a fraction R of unbound SM at a given intermediate value of $[P]_0$ can be expressed as:

$$R = \frac{S_{[P]_0} - S_{[P]_0 \to \infty}}{S_{[P]_0 \to 0} - S_{[P]_0 \to \infty}} \quad (4)$$

where $S_{[P]_0}$ is a signal at this $[P]_0$, while while $S_{[P]_0 \to 0}$ is the saturated signal for $[P]_0$ approaching zero and $S_{[P]_0 \to \infty}$ is a signal at saturating $[P]_0$ ($[P]_0 \gg K_d$). The value of $K_d$ can then be found by non-linear regression of a binding isotherm with the following equation (M. Kanoatov, V. A. Galievsky, S. M. Krylova, L. T. Cherney, H. K. Jankowski, S. N. Krylov, *Anal. Chem.* 2015, 87, 3099-3106.):

$$R = \frac{[SM]_{eq}}{[SM]_0} = \frac{([SM]_0 - [P]_0 - K_d) + \sqrt{([SM]_0 - [P]_0 - K_d)^2 + 4K_d[SM]_0}}{2[SM]_0} \quad (5)$$

The signals S may be measured in a time-point in FIG. 1C which gives great signal sensitivity to changes in $[P]_0$ and robustness with respect to small shifts of the curves along the time axis. Based on this, time corresponding to the maximum of the second peak was chosen. Equation 4 was applied to experimental data for this time point and a binding isotherm was constructed (FIG. 1D). Non-linear regression of the binding isotherm with Equation 5 was used to determine the $K_d$ value.

The in-silico study, thus, proved that LSTDLPF-based determination of $K_d$ is theoretically sound for the simplest case of signal's additivity and proportionality to $[SM]+[P-SM]$.

Example 3—In Silico Study—Quenching and Screening

Properties of signals from SM depend on the mode of detection and the nature of both P and SM. P can have a major effect on the signal of SM because it can quench SM fluorescence ("quenching") and present in the detector at the time of registration ("screening").

If optical detection is used, then intact P-SM is detected and quenching is likely to be present. On the other hand, screening by P in optical detection is unlikely. As a result, one can expect for optical detection that the signal will be determined by the following equation:

$$S = S_{[SM]} + \alpha \times S_{[P-SM]} \quad (6)$$

where $0 < \alpha < 1$ is the quenching coefficient (e.g. relative quantum yield in fluorescence detection) and $S_{[SM]}$, $S_{[P-SM]}$ are the signals from SM and P-SM respectively. While quenching may affect propagation profiles, it does not change signal additivity and, thus, no signal compensation procedure may be required before the above-described procedure of $K_d$ determination is applied to the experimental data. If mass-spectrometry (MS) is used for detection of SM, then conditions can be created to dissociate P-SM during ionization and, thus, exclude "quenching" (i.e. make $\alpha = 1$). However, the presence of P can affect ionization of SM and, hence, MS detection is likely to experience "screening". The adjusted or ideal signal time profile $S_{ideal}$ would be an additive function of the time profiles of SM and P-SM:

$$S_{ideal} = S_{[SM]} + S_{[P-SM]} \quad (7)$$

To recover the ideal signal $S_{ideal}$ we apply an operator $\hat{O}$ to the raw MS signal $S_{raw}$.

$$S_{ideal} = \hat{O} S_{raw} \quad (8)$$

$\hat{O}$ describes the mathematical compensation procedure used to recover the ideal signal. The proposed screening-compensation procedure used the following: First, P and P-SM have similar propagation profiles (FIG. 1B), which can be computer-simulated for P of a given size. Second, the concentration (and amount) of SM is constant in experiments with varying $[P]_0$, thus, typically, the areas under the temporal propagation profiles will be constant.

Based on this, a two-step screening-compensation procedure was considered: 1) multiplication ($\hat{O}_M$) of the measured profiles by the simulated profile shape of P and 2) normalization ($\hat{O}_N$) of the profiles to make areas under them equal to the area (integrals) under the experimental elution profile of SM (without any P):

$$\hat{O} := \hat{O}_N \hat{O}_M \quad (9)$$

$$\hat{O}_M = \tilde{S}_{[P]}$$

$$\hat{O}_N = \frac{\int S_{[P]=0} dt}{\int S_{raw} dt}$$

where $\tilde{S}_{[P]}$ is the normalized signal profile, i.e. the shape, of P. Combining Eq. 9 with Eq. 8 provides the instruction on how to process the raw signal in order to get the ideal signal suitable for accurate determination of $K_d$:

$$S_{ideal} = \frac{\int S_{[P]=0} dt}{\int S_{raw} dt} \tilde{S}_{[P]} S_{raw} \quad (10)$$

After obtaining $S_{ideal}$, Eq. 4 and Eq. 5 can be applied as described above. Since $S_{[P]=0}$ is utilized in $\hat{O}_N$ to compensate all the other raw signals, it cannot be used for $S_{[P]_0 \to 0}$ in the determination of R; instead, the signal profile of the smallest $[P]_0$ is used for defining $S_{[P]_0 \to 0}$.

The virtual LSTDLPF setup was used to model time-dependencies of quenching-affected signal (see FIG. 4A) and screening-affected signal (see FIG. 5A) for constant $[SM]_0$ and varying $[P]_0$. Simulation conditions for the modeling illustrated in FIGS. 4A and 4B were: internal capillary diameter=200 μm, capillary length=50 cm, flow rate of LPF=50 μL/min, EM injection by 5 μL/min for 12 s, $k_{off}=10^{-3}$ s$^{-1}$, $k_{on}=10^3$ M$^{-1}$ s$^{-1}$ ($K_d=k_{off}/k_{on}=10^{-6}$ M), $D_{SM}=500$ μm$^2$/s, $D_P=D_{P-SM}=50$ μm$^2$/s, $[SM]_0=5\times10^{-7}$ M, and $[P]_0$ ranging from about 0 μM to about 1000 μM (see FIG. 4A). Equations 4 and 5 applied to the non-compensated quenching-affected signal revealed a 0.8% of error with the real $K_d$ value (see FIG. 4B) where the quenching coefficient α equals 0.5. The screening-affected signal was adjusted with the 2-step signal compensation procedure: multiplication by the profile of P followed by area normalization (see FIG. 5C). Equations 4 and 5 applied to the compensated screening-affected signal revealed 0.3% of error with the real $K_d$ value (see FIG. 5D). Simulation conditions for the modelling are illustrated in FIGS. 5A to 5D. These computational results validated basic approaches for LSTDLPF experiments with optical and MS detection. Overall, the in-silico study proved that LSTDLPF can be used for accurately finding $K_d$ of reversible polypeptide-molecule binding provided that an experimental setup can be built to conduct experiments similar to the simulated ones.

Example 4—Experimental Implementation with Bovine Serum Albumin (BSA) and Fluorescein In an experimental implementation of the method, LSTDLPF was carried out with flow conditions inside the capillary tube being as close to LPF as possible. It is known that LPF is distorted at the capillary entrance open to a large-volume reservoir (A. Molki, L. Khezzar, A. Goharzadeh Eur. J. Phys. 2013, 34, 1127-1134). This suggested a priori that a LSTDLPF based method includes the following: 1) injection of an EM plug into the capillary at a low flow rate in order to obtain approximately a cylindrical plug shape; 2) displacement of the cylindrical EM plug from the capillary inlet at a distance much greater than the capillary diameter by introducing a plug of the buffer after the plug of EM also at a low flow rate; and 3) LSTDLPF of SM and P-SM at a high flow rate.

Figure 6B:
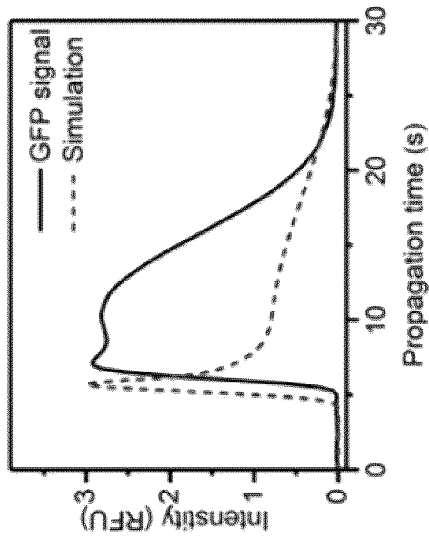
Figure 6A:
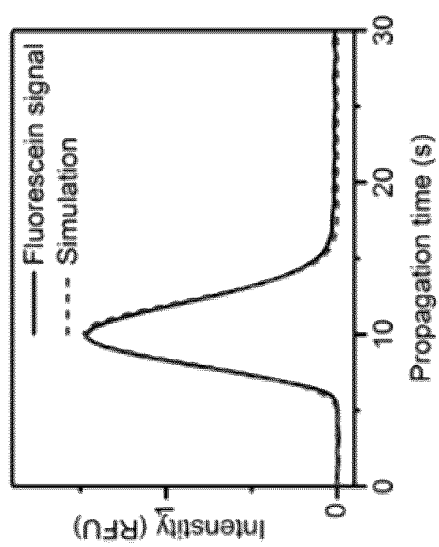
Figure 6C:
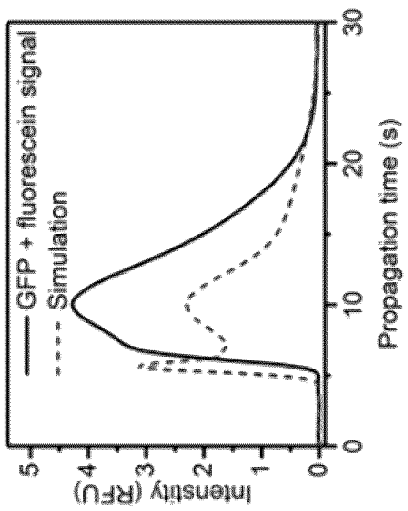

Proof-of-principle experiments for LSTDLPF were conducted using a commercial instrument which had a flow-injection system and a detector both interfaced with a capillary. A commercial capillary electrophoresis (CE) instrument with a syringe-pump injection and fluorescence detection was used. To test the quality of LSTDLPF profiles that a commercial CE instrument could produce, a mixture of green fluorescent protein (GFP) and fluorescein was used, and GFP does not bind to fluorescein. The experimental propagation profile of pure fluorescein was similar to the computer-simulated profile (FIG. 6A); however, the experimental profiles for pure GFP and the GFP-fluorescein mixture drastically differed from the computer-simulated ones (FIGS. 6B and 6C). This result suggests, without being bound by theory, that the flow-injection system in a commercial CE instrument could not support high-quality LSTDLPF. In assessing the suitability of the commercial CE instrument, the experiments were conducted with the following conditions: internal capillary diameter=150 μm, capillary length=50 cm (40 cm to detectors), propagation pressure=4 psi (corresponds to a flow rate of LPF=41 μL/min), EM injection by 0.3 psi for 10 s (corresponds to a flow rate of 3.084 μL/min), "pre-separation" plug displacement by 0.3 psi for 10 s (corresponds to a flow rate of 3.084 μL/min), [fluorescein]$_0=1\times10^{-8}$ M (FIG. 6A) and [GFP]$_0=4.63\times10^{-7}$ M (12.5 mg/L) (FIG. 6B). FIG. 6C shows the signal obtained for fluorescein/GFP mixture injected at [fluorescein]$_0=1\times10^{-8}$ M and [GFP]$_0=4.63\times10^{-7}$ M.

Figure 7:
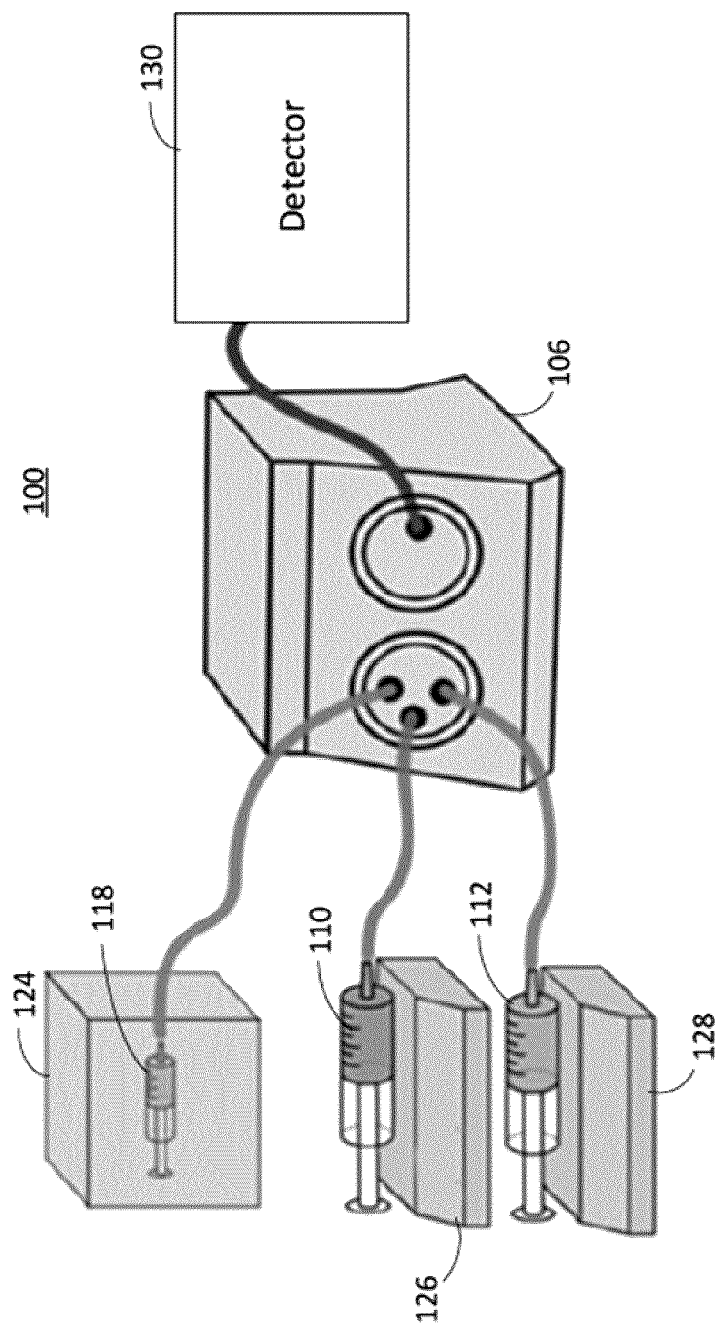
FIG. 7 illustrates a system according to an embodiment for determining the equilibrium dissociation constant of a reversible binding pair of a polypeptide and a molecule according to an embodiment.
Figure 8A:
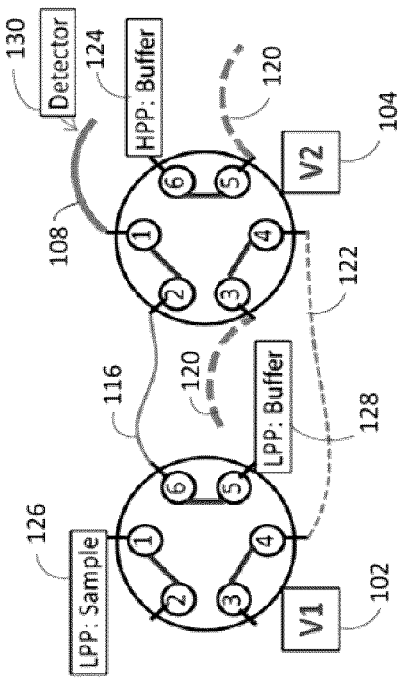
Figure 8B:
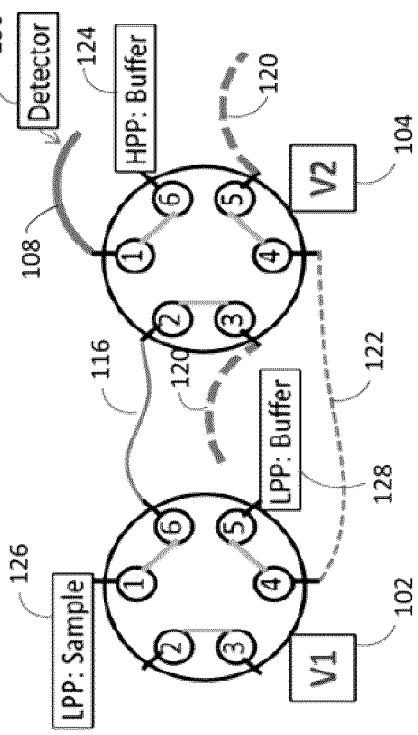
Figure 8C:
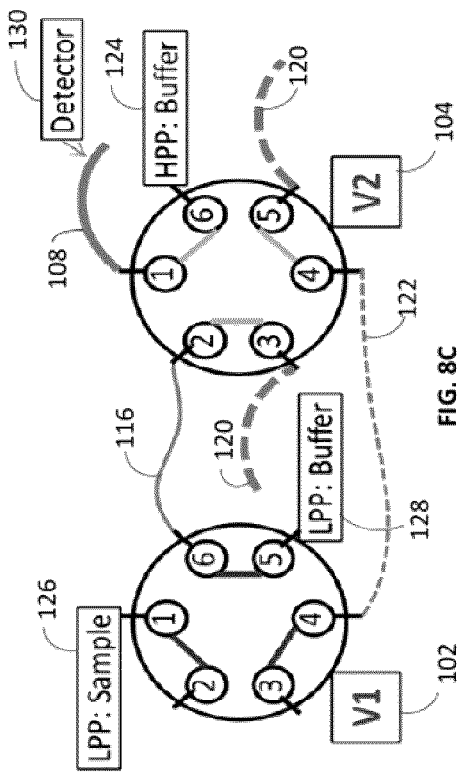

FIGS. 7 and 8A-8C illustrate one embodiment of a system for determining the equilibrium dissociation constant of reversible binding between a polypeptide and a molecule. FIG. 7 shows the system and is generally referenced by the numeral 100. This system 100 includes two injection valves 102 and 104 (shown in FIGS. 8A to 8C) inside an injection and propagation platform 106, which are controlled remotely by a controller (not shown), a high-pressure pump (HPP) 124 for the mobile phase 118, low pressure pump (LPP) 126 (or sample injector) for injecting sample 110, a low-pressure pump 128 (or mobile phase injector) for injecting mobile phase 112 at a similar low flow rate as the injected sample 110, and detector 130 (or a measurement component). FIGS. 8A to 8C show a control scheme of valves for the system 100. The control scheme shows a capillary 108 for the propagation and the detection of samples 110 by a detector 130, a loop 116 for controlling the repeatability of volume sample injected, a second or mock capillary 120 and a second or mock loop 122 that are utilized for keeping a constant back pressure typically, except for the short period when valves 102 and 104 switch from one position to another.

In some embodiments of the system 100, a single low-pressure pump could be used for the sample 110 and mobile phase 112. The sample 110 and mobile phase 112, in separate containers, could be injected using the same pump via robotics.

With respect to the LPP and the HPP, the LPP is understood to produce flow at low pressures, whereas the HPP is understood to produce flow at high pressures. In the case of the HPP 124, flow rates depend on the capillary length. For example, a capillary having a diameter of about 200 µm is about 40 cm in length, the flow rate for the HPP 124 is typically about 40 µL/min with a corresponding pressure of about 1 psi. If the capillary having a diameter of about 200 µm has a length of about 100 cm, then the flow rate is typically about 100 µL/min with a corresponding pressure of about 6 psi. In the case of the LPP 126 as it is injecting a sample into a loop, a typical flow rate is about 15 µL/min with a corresponding pressure of about 10 psi. In the case of the LPP 128 as it is injecting buffer into the capillary 108 (d=75 µm and L=23 cm) or the mock capillary 120 capillary (d=200 µm, L=50 cm), a typical flow rate is about 5 µL/min with a corresponding pressure of about 4 psi. In most embodiments, the flow rates are chosen to maintain the plug shape and laminar flow.

FIGS. 7 and 8A-C, the system 100 comprises two valves (102 and 104) inside of the inject and propagation platform 106, which are able to switch between two positions. The valves 102 and 104 have been designed and configured for the following conditions: (i) the amount of injected sample 110 was kept consistent throughout the repetitions, (ii) the injected sample 110 was introduced at a low flow rate in the capillary 108 in order to obtain plug shape with an insignificant front curvature, (iii) a mobile phase 112 was introduced after the sample 110 at the same flow rate, (iv) the propagation of the sample 110 was performed quickly in order to perform the fast separation between SM and P-SM, and (v) the flow rates of injections and of propagations remained constant despite switching of the valves 102 and 104.

The system operates in the following manner. A loop 116 is utilized in order to deliver the same amount of sample consistently. For the experiments, the loop 116 had a volume of 1 µL ($V_{loop}$). To complete the filling of the loop, the sample 110 was introduced into the loop at 15 µL/min during 12 s ($t_1$) by using a sample low pressure pump 126, which represents 3 times the volume of the loop (FIG. 8A). The low-pressure pump 126 may be, but is not limited to, a syringe pump or a peristaltic pump. While the loop is being filled as depicted in FIG. 8A, the capillary 108 is conditioned with the mobile phase 118 at high flow rate by using a high-pressure pump 124. This high flow rate corresponds to the flow rate utilized during the propagation and will be noted $Q_{prop}$ afterward.

The low-pressure pump 126 utilized for the injection of the sample 110 at a low flow rate may be a syringe pump 126. The low-pressure pump (LPP) 128 may be, but is not limited to, a syringe pump or a peristaltic pump, and delivers continuously the mobile phase (e.g. buffer 112).

In the configuration illustrated in FIGS. 8A-8C, the mobile phase (e.g. buffer 112) is delivered in a mock loop 122 and a mock capillary 120, whose roles are to mimic the microfluidic pathway utilized for the sample injection and to provide constant back pressures for the LPP 128 and for the HPP 124. Maintaining back pressure in LPP 128 and HPP 124 allows for the pressure within the system 100 to be consistent especially during the switching of the valves 102 and 104. As seen in FIGS. 6A to 6C, with generic instrumentation, the front of the pulse has a slope, which is attributed to the ramp-up pressure of the CE instrumentation. To generate a pressure pulse with near-vertical slopes, the system pump would have to be running constantly in a steady state. The system 100 utilizes different pressures at different times which is realized by switching valves 102 and 104 rather than turning pumps on or off or changing their pressures of flow rates. Switching time is short and does not cause a pump to deviate from the steady state. Delivering mobile phase 112 in the mock loop 122 and mock capillary 120 such that the back pressure is constant except for the short switching times. The mock capillary 120 empties to waste (not shown). The flow rate of the LPP 128 was 5 µL/min and will be noted as $Q_{inj}$. Custom software written in Labview® was utilized to control the low and high-pressure pumps 128 and 124, respectively, positions of each valve, and the duration of each position. The duration of the step described in FIG. 8A corresponds to the time to fill the loop ($t_1$).

One skilled in the art would understand how to choose a suitable mobile phase depending on the detector 130 and the intended environment for SM, as outlined above.

The injection of the sample is illustrated in FIG. 8B. The positions of both valves 102 and 104 have been switched. In this configuration, the low-pressure pump 128 delivered the mobile phase 112 via the injection loop 116 which contained the sample or equilibrium mixture (EM) 110. Pushed by the mobile phase, the sample 110 was consequently introduced into the capillary at $Q_{inj}$=5 µL/min and the time for moving the EM 110 from the loop into the inlet of the capillary 108, referred to as $t_{inj}$, was approximately 12 s $V_{loop}/Q_{inj}$). Following the injection of the sample 110 into the capillary 108, mobile phase 112 was introduced into the capillary 108 by the LPP 128 for a duration of approximately 12 s ($t_2-t_{mi}$) without any changes in the system configuration (e.g. without switching the valves). Therefore, FIG. 8B was set to have a total duration of $t_2$=24 s with LabVIEW software. Experimental acquisition was triggered at the beginning of the step illustrated in FIG. 8B. Therefore, the simulations performed in parallel start equally when the EM 110 was injected.

The propagation of the sample or EM 110 was performed during the configuration illustrated in FIG. 8C with the switch of valve 104. The mobile phase or buffer 118 in the capillary 108 was then delivered by the HPP 124 at a higher flow rate noted as $Q_{prop}$. $Q_{prop}$ was adjusted in order to let the molecule diffuse transversely or radially across the capillary 108 during the detection time and varies as a function of the capillary length to the detector 130 utilized in the system. In this embodiment, valve 102 was not switched during the propagation, as this allowed the mobile phase LPP 128 to flush the injection loop 116 during the propagation and to save time without having a dedicated flush step. The duration of the 3 steps illustrated in FIGS. 8A-8C was around 1.5 minutes.

The system described in FIGS. 7 and 8A-8C provided agreement between experimental and simulated LSTDLPF profiles for the GFP/fluorescein pair (FIGS. 9A-9C). Experimental conditions for such profiles were: internal capillary diameter=150 µm, capillary length=50 cm (40 cm to detector 130), flow rate of LPF=41 µL/min, EM injection by 3.1 µL/min for 10 s, "pre-separation" plug displacement by 3.1 µL/min for 10 s, [fluorescein]$_0$=1×10$^{-7}$ M (FIG. 9A) and

[GFP]$_0$=4.63×10$^{-7}$ M (12.5 mg/L) (FIG. 9B), and FIG. 9C shows the signal obtained for GFP/fluorescein mixture injected at [fluorescein]$_0$=1×10$^{-7}$ M and [GFP]$_0$=4.63×10$^{-7}$ M.

Figure 10:
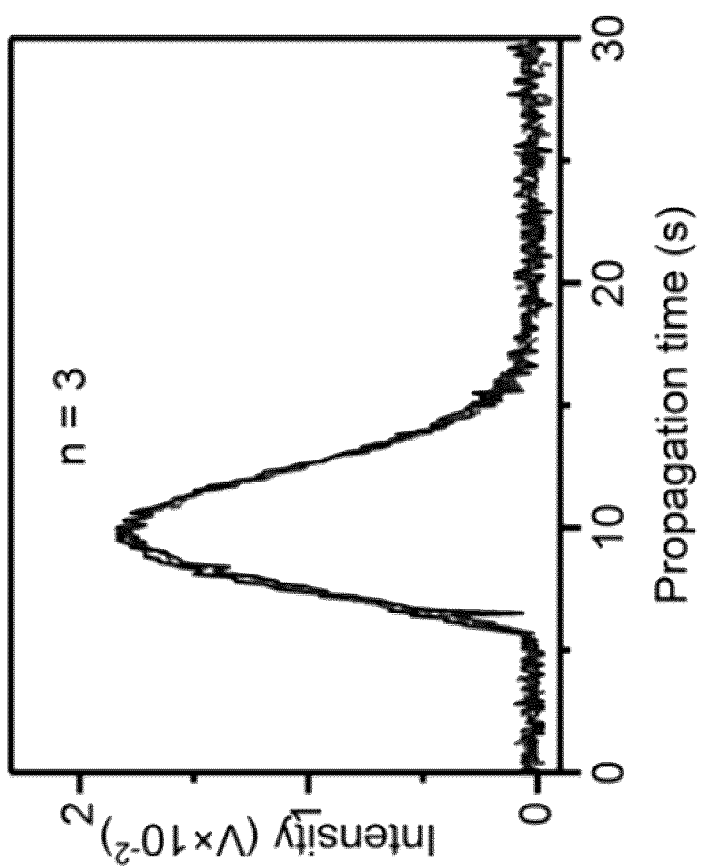
FIG. 10 illustrates reproducibility of fluorescein signal at $[\text{fluorescein}]_0=1\times10^{-7}$ M with fluorescence detection obtained by a method for determining the equilibrium dissociation constant of a reversible binding according to an embodiment.

In addition to an agreement between experiment and simulation, the system illustrated in FIGS. 7 and 8A-8C provided day-to-day reproducibility (FIG. 10). This experimental setup was, thus, used to demonstrate LSTDLPF-based experimental determination of K$_d$. Experimental conditions were: internal capillary diameter=150 μm, capillary length=50 cm (40 cm to detector), flow rate of LPF=41 μL/min, EM injection by 3.1 μL/min for 10 s, "pre-separation" plug displacement by 3.1 μL/min for 10 s, [fluorescein]$_0$=1×10$^{-7}$ M.

The first set of experiments were conducted with a fluorescence detector and with a molecular pair of BSA and fluorescein that are known to bind with a K$_d$ value of ~30 μM (L. O. Andersson, A. Rehnstrom, D. L. Eaker *Eur. J. Biochem.* 1971, 20, 371-380). The concentration of fluorescein was kept constant while the concentration of BSA was varied. Experimental conditions were: internal capillary diameter=200 μm, capillary length=60 cm (50 cm to detector), flow rate of LPF=50 μL/min, loop's internal diameter=75 μm, loop's length=22.7 cm, loop's volume=1 μL, EM injection by 5 μL/min for 12 s (plug length=3.2 cm); "pre-separation" plug displacement by 5 μL/min for 12 s (3.2 cm displacement); [fluorescein]$_o$=200 nM; [BSA]$_0$ ranged from 0 to 1 mM; and the buffer was 30 mM ammonium acetate buffer at pH 7.5.

Figure 11B:
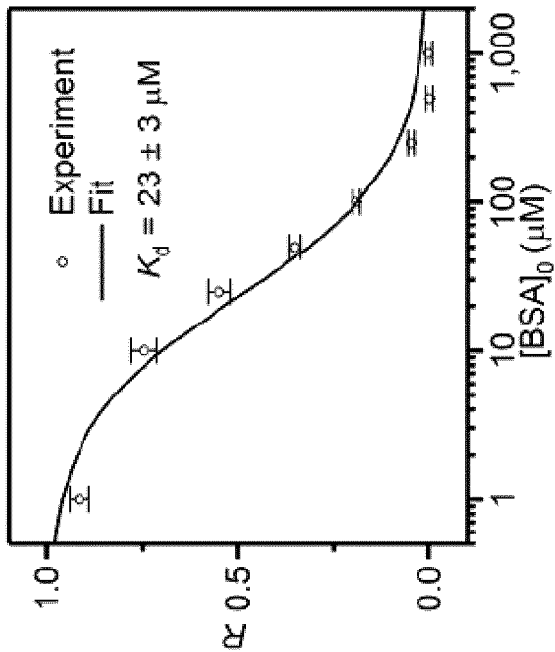
FIGS. 11A and 11B illustrate LSTDLPF-fluorescence-based determination of $K_d$ for a reversible binding pair of BSA and fluorescein according to an embodiment.
Figure 11A:
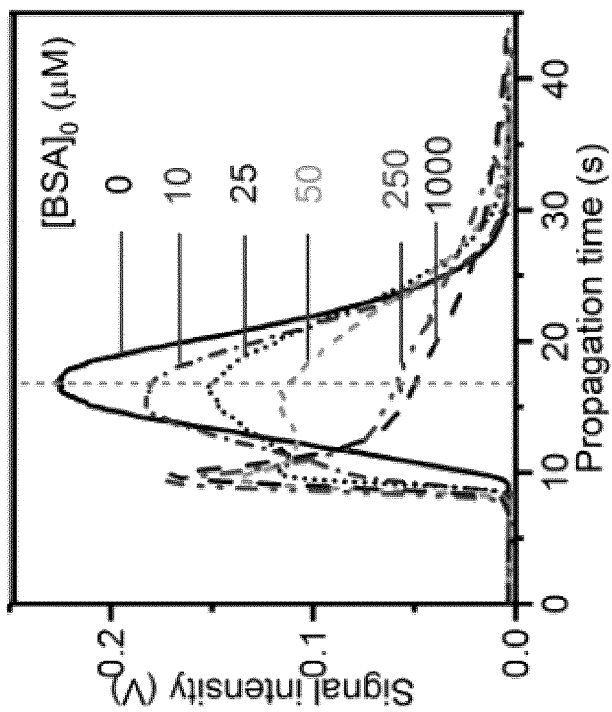
Figures 13A, 13B:
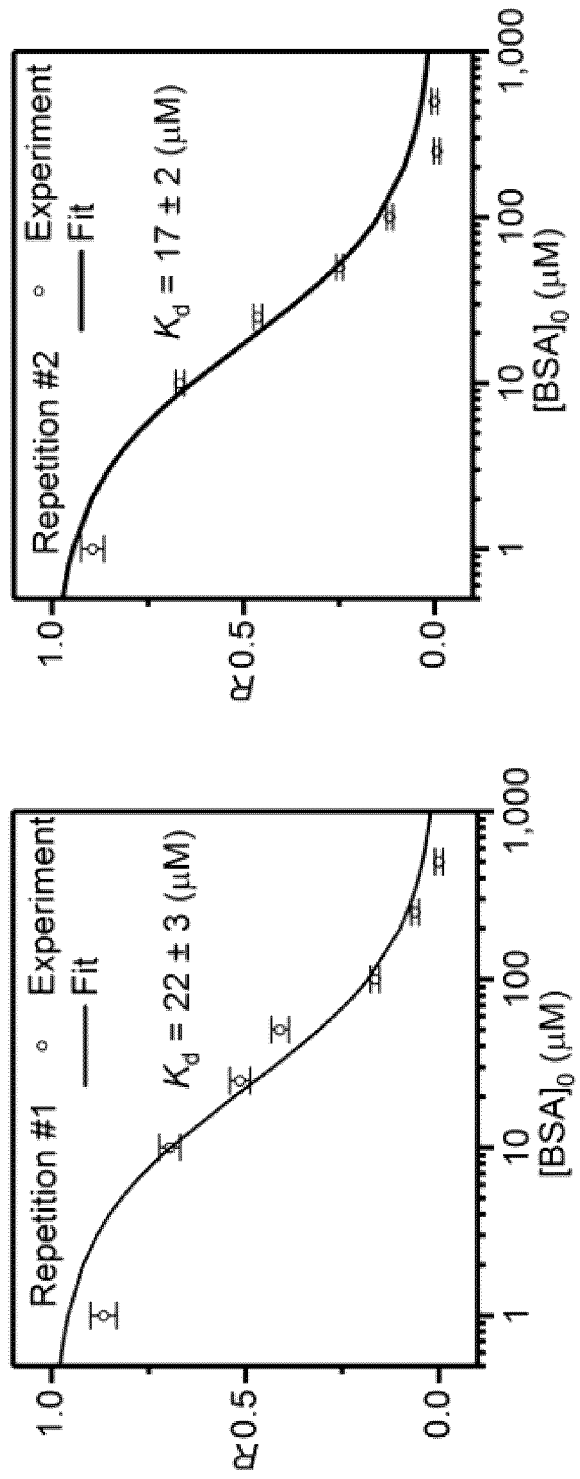
FIGS. 13A and 13B illustrate reproducibility of fluorescein/BSA $K_d$ determination by LSTDLPF-based methods according to embodiments.

The obtained temporal propagation profiles (FIG. 11A) have a typical LSTDLPF bimodal shape with gradual increase in the first peak upon increasing [BSA]$_0$. The results obtained from such experiments showed repeatability (see FIGS. 12A-12I). A binding isotherm was built by applying Equation 4 to the data shown in FIG. 11A. Non-linear regression of the isotherm with Equation 5 gave K$_d$=23±3 μM. The error represents the standard deviation between experimental points and the non-linear regression performed with OriginPro software. The experiment was reproduced on two different days (binding isotherms for the 2 additional experiments are shown in FIGS. 13A and 13B), and the result of this triplicate experiment gave a global K$_d$=20±2 μM demonstrating precision and ruggedness. The error represents the standard deviation obtained with the three experiments performed on different days.

Example 5—Experimental Implementation with Mass Spectrometry

Figure 14B:
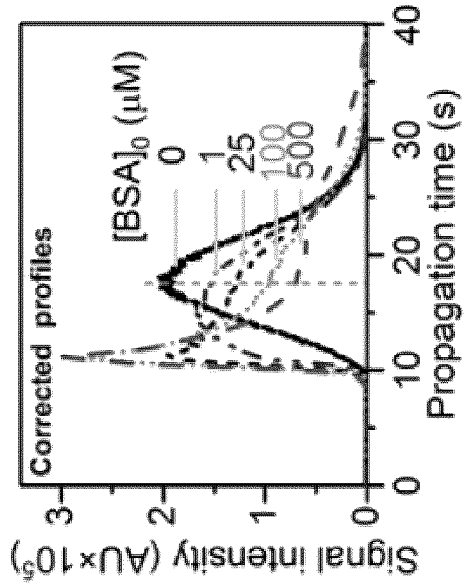
FIGS. 14A-14C illustrate experimental results for fluorescein/BSA interaction studies with mass-spectrometry detection using LSTDLPF-based $K_d$ determination methods according to embodiments
Figure 14C:
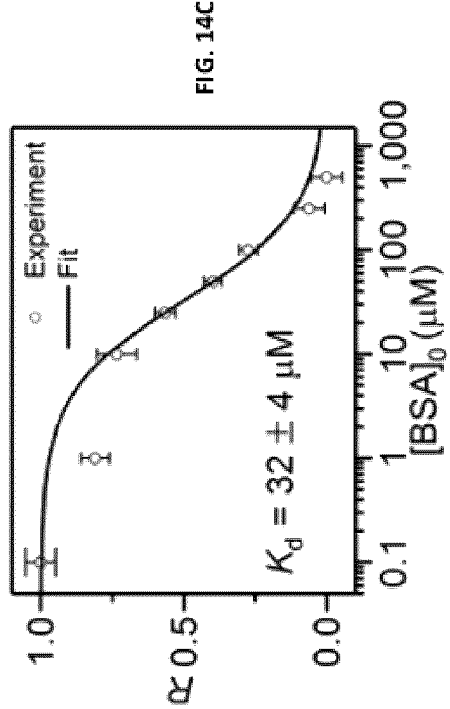
Figure 14A:
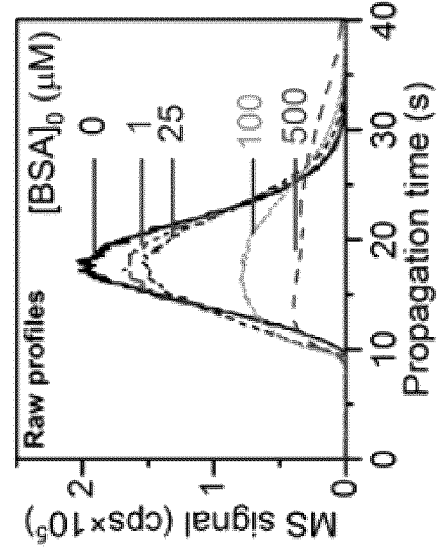
Figure 16B:
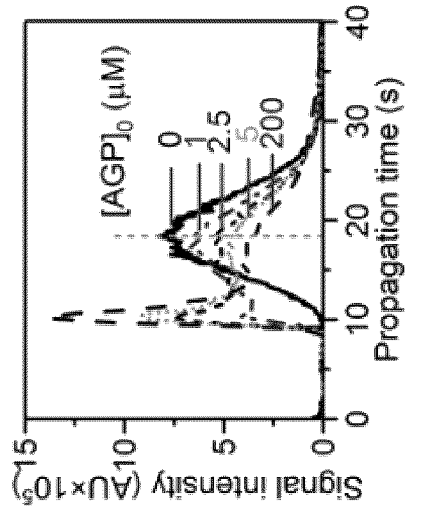
FIGS. 16A-16C illustrate experimental results for alprenolol/α1-acid glycoprotein (AGP) interaction studies with mass-spectrometry detection using LSTDLPF-based $K_d$ determination methods according to embodiments.
Figure 16C:
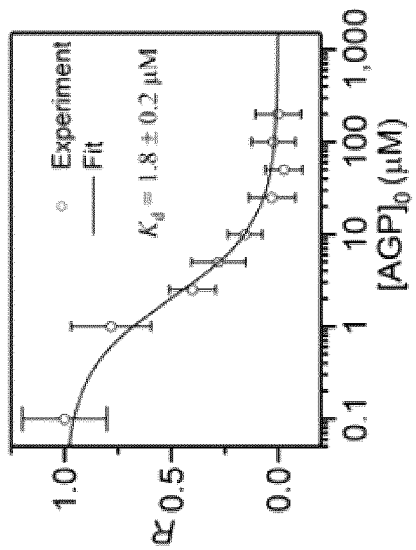
Figure 16A:
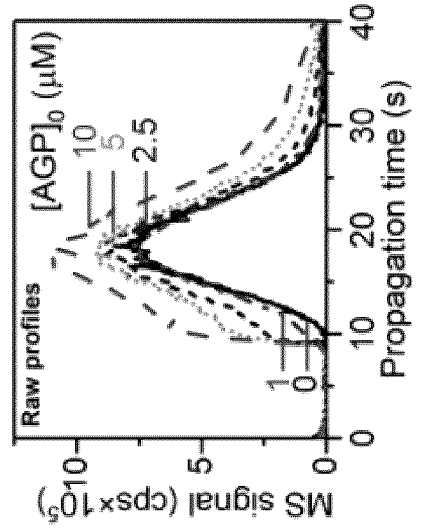

In another embodiment, the LSTDLPF setup was coupled with a mass-spectrometry (MS) detector. To facilitate complete dissociation of SM during ionization, an atmospheric pressure chemical ionization (APCI) ionization source was utilized (FIGS. 14A, 16A). The LSTDLPF-MS tandem was first used to study the same BSA/fluorescein binding pair. Experimental conditions were: internal capillary diameter=200 μm, capillary length=100 cm, flow rate of LPF=100 μL/min. loop's internal diameter=75 μm, loop's length=22.7 cm, loop's volume=1 μL, EM injection into the capillary followed by EM displacement from the capillary opening by 5 μL/min for 12 s (EM plug length=3.2 cm); "pre-separation" plug displacement by 5 μL/min for 12 s (3.2 cm displacement); [fluorescein]$_0$=200 nM; and buffer was 30 mM ammonium acetate buffer at pH 7.5. MS experiments were carried out on a QTRAP 6500+ time-of-flight (Q-TOF) instrument (Sciex, Concord, ON, Canada) with a commercial Turbo V APCI ionization source. The optimal acceleration and focusing conditions were achieved by using 60 V declustering potential at 525° C. and 90 psi gas pressure. The analyses were performed in positive mode and scanned m/z 287 Da for fluorescein. The results were analyzed by using Analyst® QS 2.0 software.

Figure 17B:
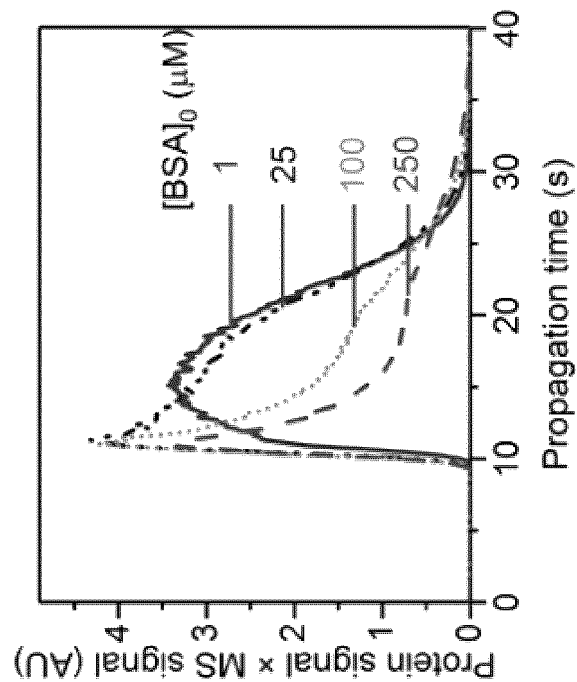
FIGS. 17A and 17B illustrate signal compensation procedures applied to fluorescein/BSA signals obtained by LSTDLPF with mass spectrometry detection according to embodiments.
Figure 17A:
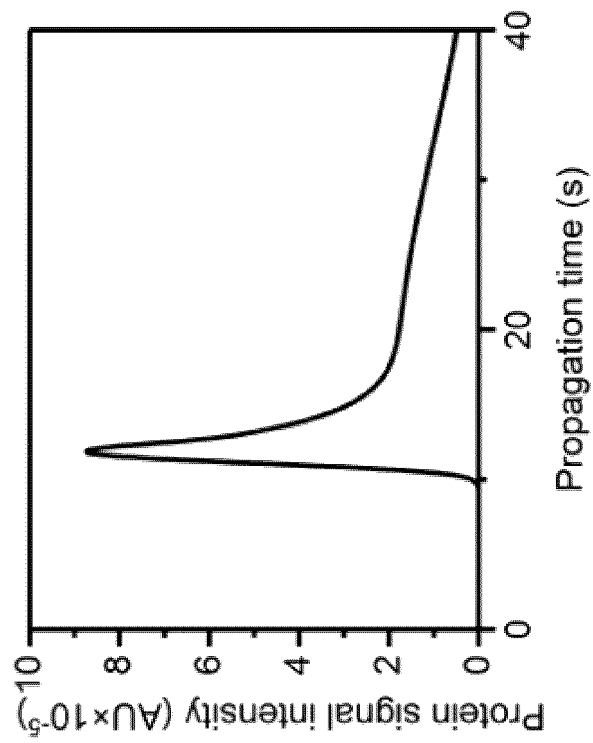
Figure 18B:
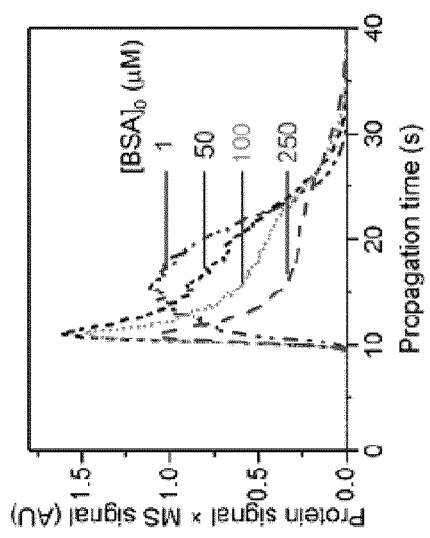
FIGS. 18A-18D illustrate signal compensation procedures applied to fluorescein/BSA signals obtained by LSTDLPF with mass spectrometry detection according to embodiments.
Figure 18D:
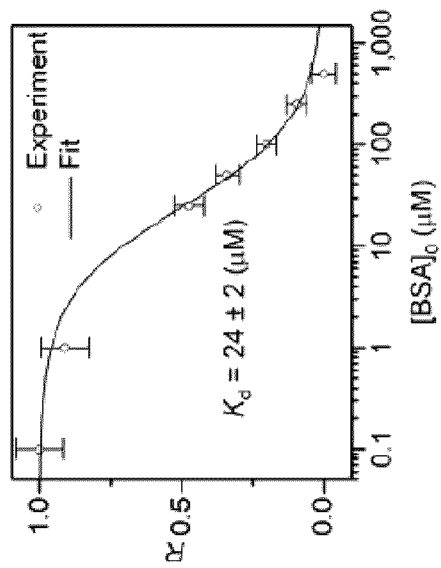
Figure 18A:
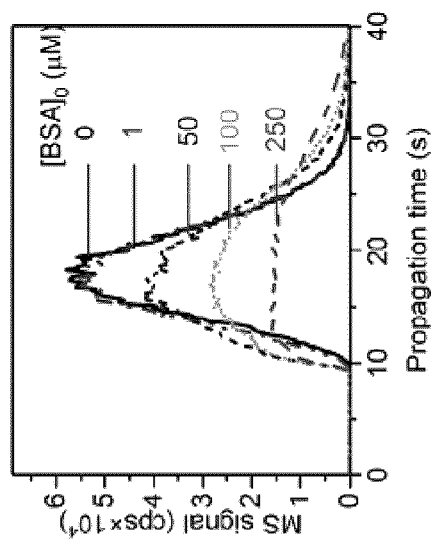
Figure 18C:
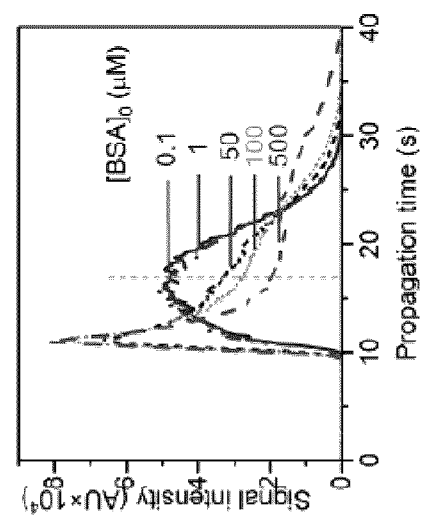

The MS signal decreased with increasing [BSA]$_0$ (FIG. 14A), due to the screening effect. The results presented repeatability (see FIGS. 15A-15I). Experimental conditions were: internal capillary diameter=200 μm, capillary length=100 cm, flow rate of LPF=100 μL/min. loop's internal diameter=75 μm, loop's length=22.7 cm, loop's volume=1 μL, EM injection by 5 μL/min for 12 s (plug length=3.2 cm); "pre-separation" plug displacement by 5 μL/min for 12 s (3.2 cm displacement); [fluorescein]$_0$=200 nM; [BSA]$_0$ ranged from 0 to 1 mM; and buffer was 30 mM ammonium acetate buffer at pH 7.5. MS experiments were carried out on a QTRAP 6500+ time-of-flight (Q-TOF) instrument (Sciex, Concord, ON, Canada) with a commercial Turbo V APCI ionization source. The optimal acceleration and focusing conditions were achieved by using 60 V declustering potential at 525° C. and 90 psi gas pressure. The analyses were performed in positive mode and scanned m/z 287 Da ion. The results were analyzed by using Analyst® QS 2.0 software The 2-step screening compensation procedure (see FIG. 17) was applied that resulted in compensated propagation profiles (FIG. 14B). Equation 4 was then used to provide the binding isotherm and Equation 5 was used to find K$_d$=32±4 μM via non-linear regression of the experimental data (FIG. 14C). The experiment was reproduced on another day (FIG. 18) and gave K$_d$=24±2 μM. The weighted average of K$_d$, from the previous two K$_d$ measurements, is K$_d$=26±2 μM, which agrees with the value obtained with fluorescence detection of K$_d$=20±2 μM.

The LSTDLPF-MS tandem was then used in K$_d$ determination for a reversible binding pair of alprenolol and α1-acid glycoprotein (AGP).

MS experiments were carried out on a QTRAP 6500+ time-of-flight (Q-TOF) instrument (Sciex, Concord, ON, Canada) with a commercial Turbo V APCI ionization source. The optimal acceleration and focusing conditions were achieved by using 60 V declustering potential at 525° C. and 90 psi gas pressure. The analyses were performed in positive mode and scanned m/z 250 Da for alprenolol. The results were analyzed by using Analyst® QS 2.0 software. The propagation profiles obtained for [alprenolol]$_0$=500 nM and varying [AGP]$_0$ were reproducible (FIGS. 19A-19J). Experimental conditions were: internal capillary diameter=200 μm, capillary length=100 cm, flow rate of LPF=100 μL/min., loop's internal diameter=75 μm, loop's length=22.7 cm, loop's volume=1 μL; EM injection by 5 μL/min for 12 s (plug length=3.2 cm); "pre-separation" plug displacement by 5 μL/min for 12 s (3.2 cm displacement); [AGP]$_0$ ranged from 0 to 1 mM; buffer was 30 mM ammonium acetate buffer at pH 7.5.

In this case, the screening phenomenon was characterized by enhancing signal of alprenolol with growing [AGP]$_0$, (FIG. 16A). The 2-step screening compensation procedure was then applied that resulted in compensated propagation profiles (FIG. 16B). Equation 4 was then used to provide the binding isotherm and Equation 5 was used to find K$_d$=1.8±0.2 μM (FIG. 16C). The determined K$_d$ result is consistent with those found in the literature: 2.1±0.3 μM (J. Bao, S. M. Krylova, D. J. Wilson, O. Reinstein, P. E. Johnson, S. N. Krylov, *ChemBioChem* 2011, 12, 2551-2554) and 1.6±0.1 μM (H. Imamura, T. Komori, A. Ismail, A. Suenaga, M. Otagiri, *Chirality* 2002, 14, 599-603). The method is also characterized by an acceptable reproducibility. For measurements performed on a different day, $K_d=4.1\pm0.8$ µM (see FIGS. 20A-20D) was obtained.

Figure 21B:
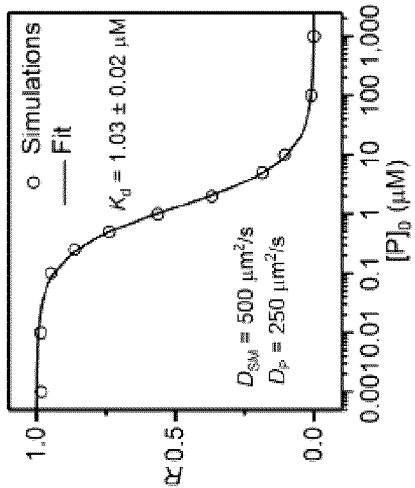
Figure 21A:
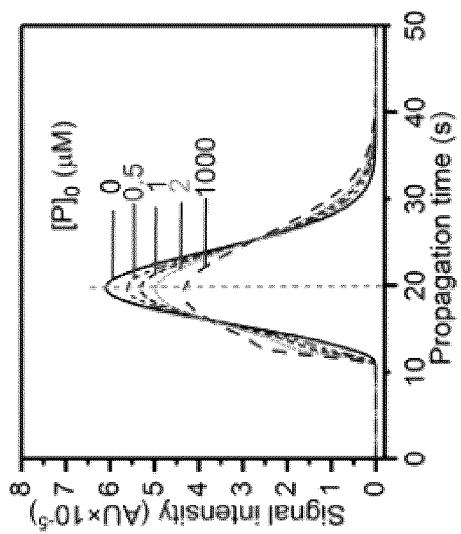

FIGS. 21A-21B illustrate a simulation of $K_d$ determination by LSTDLPF according to an embodiment in which FIG. 21A illustrates five simulated temporal propagation profiles of [SM]+[P-SM] at constant $[SM]_0=0.5$ µM while varying $[P]_0$ in EM and FIG. 21B is the binding isotherm obtained using the data illustrated in FIG. 21A, where 2× difference in diffusion coefficients of SM and P was used in finding $K_d$. These figures illustrate that the method can be used for finding $K_d$ of a reversible binding pair in which, for example, SM is a protein which has a molecular weight that is approximately 8× lower than a protein P, which correlates to 2× difference in diffusion coefficients.

The examples and corresponding diagrams used herein are for illustrative purposes only. The principles discussed herein with reference to determination of equilibrium dissociation constants can be implemented in other systems. Different configurations and terminology can be used without departing from the principles expressed herein. For instance, steps, equipment, components, and modules can be added, deleted, modified, or re-arranged without departing from these principles.

Specific examples of systems and methods have been described herein for purposes of illustration. These are only examples. The methods and systems provided herein can be applied to systems other than the examples described above. Many alterations, modifications, additions, omissions and permutations are possible within the practice of this invention, and includes variations on described implementations that would be apparent to the skilled addressee, including variations obtained by: replacing features, elements and/or acts with equivalent features, elements and/or acts; mixing and matching of features, elements and/or acts from different implementations; combining features, elements and/or acts from implementations as described herein with features, elements and/or acts of other technology; omitting and/or combining features, elements and/or acts from described implementations. Where a component is referred to above, unless otherwise indicated, reference to that component should be interpreted as including as equivalents of that component, any component which performs the function of the described component (i.e., that is functionally equivalent), including components which are not structurally equivalent to the disclosed structure which performs the function in the illustrated exemplary implementations.

Implementations as described herein can include controllers implemented using specifically designed hardware, configurable hardware, programmable data processors configured by the provision of software (which can optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, single-chip computers, and the like. For example, one or more data processors in a control circuit for a device can implement methods as described herein by executing software instructions in a program memory accessible to the processors.

It is understood that the terminology used herein is for the purpose of describing particular embodiments/aspects only, and is not intended to be limiting. Many patent applications, patents, and publications are cited herein to assist in understanding the aspects described. All such references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. "Connected," "coupled," or any variant thereof means any connection or coupling, either direct or indirect, between two or more elements; the coupling or connection between the elements can be physical, logical, or a combination thereof. "Herein," "above," "below," and words of similar import, when used to describe this specification shall refer to this specification as a whole and not to any particular portions of this specification.

It will be understood that any component defined herein as being included may be explicitly excluded from the claimed invention by way of proviso or negative limitation.

In addition, all ranges given herein include the end of the ranges and also any intermediate range points, whether explicitly stated or not.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The abbreviation, "e.g." is derived from the Latin exempli gratia, and is used herein to indicate a non-limiting example. Thus, the abbreviation "e.g." is synonymous with the term "for example." The word "or" is intended to include "and" unless the context clearly indicates otherwise.

While the foregoing embodiments have been described in some detail for purposes of clarity and understanding, it will be appreciated by one skilled in the art, from a reading of the disclosure that various changes in form and detail can be made without departing from the true scope of the invention in the appended claims.

What is claimed is:

1. A method for determining an equilibrium dissociation constant ($K_d$) of a reversible binding pair of a first compound and a second compound, the method comprising:
   injecting a sample into a capillary tube via one or more valves, wherein the sample comprises the first compound, the second compound, and a first compound-second compound complex;
   injecting a mobile phase into the capillary tube via said one or more valves, the sample flowing through the capillary tube under laminar flow conditions, wherein the second compound and the first compound-second compound complex is separated from the first compound by transverse diffusion;
   measuring time dependence of a signal that is proportional to the concentration of the first compound, both unbound and bound to the second compound using a measurement component; and
   determining the equilibrium dissociation constant based on the measured signal versus time dependence;
   wherein the $K_d$ is determined by non-linear regression of a binding isotherm with the following equation:

$$R = \frac{\left([SM]_0 - [P]_0 - K_d + \sqrt{([SM]_0 - [P]_0 - K_d)^2 + 4K_d[SM]_0}\right)}{2[SM]_0}$$

wherein:
   R is the ratio of concentration of the unbound first compound compared to the total concentration of the first compound in the sample;
   $[P]_0$ is the total second compound concentration in the sample; and
   $[SM]_{eq}$ is the equilibrium concentration of the first compound in the sample; and
   $[SM]_0$ is the total concentration of the first compound in the sample.

2. The method of claim 1, further comprising injecting a mobile phase into a second capillary tube, wherein the second capillary tube mimics the capillary tube, creating a constant back pressure for the mobile phase injector.

3. The method of claim 1, wherein the injecting of the sample is executed by a sample injector comprising a low-pressure pump, optionally, wherein the low-pressure pump is a syringe pump.

4. The method of claim 1, wherein the injecting of the mobile phase is executed by a mobile phase injector comprising a high-pressure pump, optionally, wherein the high pressure pump is a high-pressure liquid chromatography pump.

5. The method of claim 2, wherein the injecting of the mobile phase into the second capillary tube is done using a second low pressure pump, creating a constant back pressure for the mobile phase injector and the second low pressure pump.

6. The method of claim 1, wherein the injecting of the sample and the injecting of the mobile phase comprises:
   injecting into the capillary tube the sample at a flow rate less than or about Q/10;
   injecting into the capillary tube the mobile phase at a flow rate less than or about Q/10 to displace the sample from the capillary tube's inlet at a distance greater than the capillary tube's diameter; and
   propagating the sample under the laminar flow conditions at a flow rate of $Q=\pi LD_{SM}$, wherein Q is the flow rate, L is the capillary tube's length, and $D_{SM}$ is the diffusion coefficient of the first compound, or
   wherein the injecting of the sample and the injecting of the mobile phase comprises:
   injecting into the capillary tube the sample at a flow rate less than or about Q/10 to obtain approximately a uniform plug shape;
   injecting into the capillary tube a plug of a mobile phase at a flow rate less than or about Q/10 to displace the uniform plug from an inlet of the capillary tube at a distance greater than the capillary tube's diameter; and
   propagating the sample under the laminar flow conditions at a flow rate of $Q=\pi LD_{SM}$, wherein Q is the flow rate, L is the capillary tube's length, and $D_{SM}$ is the diffusion coefficient of the first compound.

7. The method of claim 6, wherein the sample is displaced without substantively affecting the plug shape, optionally, a cylindrical plug shape.

8. The method of claim 1, wherein a separation time $t_{sep}$ of the unbound first compound and the first compound bound to the second compound is determined using the formula $t_{sep}=d^2/(4D_{SM})$ wherein d is the diameter of the capillary tube, and the $D_{SM}$ is the diffusion coefficient of the first compound, optionally, wherein the separation time $t_{sep}$ correlates with transverse diffusion of the first compound, optionally, wherein the value of d is from about 10 to about 300 μm, $D_{SM}$ is from about 100 to about 1000 μm²/s, and separation time $t_{sep}$ is from about 0.025 to about 225 s or from about 0.2 to about 20 s.

9. The method of claim 1, further comprising compensating for the second compound's effect on the signal of the first compound, wherein the second compound's effect on the signal of the first compound is compensated by the equation:

$$S_{ideal}=\hat{O}S_{raw}$$

wherein:
   $S_{ideal}$ is an adjusted signal time profile, $S_{raw}$ is a raw signal from the measurement component and:

$$\hat{O} := \hat{O}_N \hat{O}_M$$

$$\hat{O}_M = \tilde{S}_{[P]}$$

$$\hat{O}_N = \frac{\int S_{[P]=0} dt}{\int S_{raw} dt}$$

wherein M in said $\hat{O}_M$ is multiplication, and N in said $\hat{O}_N$ is normalization.

10. The method of claim 1, wherein the laminar flow conditions are maintained by pressure injection of the mobile phase into the capillary tube.

11. The method of claim 1, wherein the laminar flow conditions have a flow rate from about 0.2 μL/min to about 600 μL/min, about 50 μL/min to about 400 μL/min, about 50 μL/min to about 200 μL/min, or about 50 μL/min to about 100 μL/min.

12. The method of claim 1, wherein the reversible binding pair is capable of forming an equilibrium mixture of the first compound, the second compound, and a non-covalent complex of the first compound and the second compound.

13. The method of claim 1, wherein the first compound is a therapeutic agent.

14. The method of claim 1, wherein the second compound is a polypeptide, optionally, a protein.

15. The method of claim 1, wherein a molecular weight of the first compound is less than the molecular weight of the second compound, optionally, wherein the first compound has a molecular weight less than about 1 kDa and/or the second compound has a molecular weight less than about 100 kDa, and optionally, wherein the second compound has a molecular weight from about 5 kDa to about 100 kDa.

16. The method of claim 1, wherein the first compound has a diffusion coefficient that is greater than the diffusion coefficient of the second compound, wherein the diffusion coefficient of the first compound is at least about 2× greater than the diffusion coefficient of the second compound, at least about 5× greater than the diffusion coefficient of the second compound, or at least about 8× greater than the diffusion coefficient of the second compound.

17. The method of claim 16, wherein the diffusion coefficient of the first compound is from about 100 $\mu m^2/s$ to about 1000 $\mu m^2/s$ or from about 500 $\mu m^2/s$ to about 700 $\mu m^2/s$.

18. The method of claim 1, wherein the sample is an equilibrium mixture comprising the first compound, the second compound, and a first compound-second compound complex.

19. The method of claim 1, wherein the measurement component is a detector, optionally, wherein the detector is a mass spectrometer or an optical spectrometer, optionally, wherein the mass spectrometer comprises an atmospheric pressure chemical ionization (APCI) mass spectrometer or wherein the optical spectrometer comprises light-absorbance spectrometer or a fluorescence spectrometer.

20. The method of claim 1, wherein the sample further comprises a mobile phase selected to optimize separation of the first compound from the second compound and the first compound-second compound complex, optionally, wherein the mobile phase has a viscosity that optimizes separation of the first compound from the second compound and the first compound-second compound complex.

21. The method of claim 1, wherein the second compound and the first compound-second compound complex have similar diffusion coefficients and have similar bimodal propagation profiles and, optionally, wherein the first compound has a unimodal propagation profile.

22. The method of claim 1, wherein the mobile phase is a liquid mobile phase, optionally a buffer, and optionally, wherein the mobile phase is similar to a physiological environment without compromising the detection of the first compound.

23. The method of claim 1, wherein the capillary tube has an inner diameter less than about 1 mm, less than about 700 $\mu m$, less than about 400 $\mu m$, less than about 200 $\mu m$, less than about 100 $\mu m$, less than about 50 $\mu m$, or from about 10 $\mu m$ to about 300 $\mu m$.

24. The method of claim 1, wherein the capillary tube is selected such that adsorption of the first compound, the second compound, and the first compound-second compound complex is minimized.

25. The method of claim 1, wherein the capillary tube has an inner wall that is relatively smooth and/or non-porous, optionally, coated with a flexible coating material.

26. The method of claim 25, wherein the coating material is fused silica, a polymer, and/or resin, optionally, wherein the material is selected from the group consisting of polyimide, silicone, polyacrylate, aluminum, fluoropolymer, polystyrene, fused silica, polymethylmethacrylate, fluoroplastic, and acrylic.

27. The method of claim 1, wherein the capillary tube has a length L that is proportional to a flow rate Q under the laminar flow conditions, wherein the proportion is determined by the formula $Q=\pi L D_{SM}$, where $D_{SM}$ is the diffusion coefficient of the first compound and/or wherein the capillary tube has a diameter d greater than $\rho L D_{SM}/(500\eta)$ when Reynolds number is less than about 2000, wherein $\rho$ and $\eta$ are the density and dynamic viscosity of the mobile phase injected into the capillary tube to maintain laminar flow conditions, respectively.

28. The method of claim 1, wherein the mobile phase is injected continuously under constant pressure into the capillary tube and/or wherein the mobile phase is injected at a pressure from about 0.2 psi to about 3000 psi.

29. The method of claim 1, wherein the method is suitable for high throughput screening.

30. The method of claim 1, wherein the method is suitable for screening the first compound or the second compound for their ability to form a first compound-second compound complex.

31. The method of claim 1, wherein said one or more valves are two valves.

32. The method of claim 1, wherein the $K_d$ is at least about 1 nM or from about 1 nM to about 40 $\mu M$.

33. The method of claim 1, further comprising injecting the sample through an injector loop.

34. The method of claim 1, wherein the first compound and the second compound are both polypeptides, optionally, wherein the polypeptides are proteins.

* * * * *